US011179074B1

(12) United States Patent
Lash et al.

(10) Patent No.: US 11,179,074 B1
(45) Date of Patent: Nov. 23, 2021

(54) PROBE FOR MONITORING WET OR MOIST ENVIRONMENTS

(75) Inventors: Robert E. Lash, Redwood City, CA (US); Larry C. Heaton, II, Pleasanton, CA (US); Alex Keller, Manhasset, NY (US)

(73) Assignee: ViOptix, Inc., Newark, CA (US)

( * ) Notice: Subject to any disclaimer, the term of this patent is extended or adjusted under 35 U.S.C. 154(b) by 604 days.

(21) Appl. No.: 12/479,359

(22) Filed: Jun. 5, 2009

Related U.S. Application Data

(63) Continuation-in-part of application No. 29/336,797, filed on May 8, 2009, now Pat. No. Des. 618,803.

(51) Int. Cl.
*A61B 5/1455* (2006.01)
*A61B 5/00* (2006.01)

(52) U.S. Cl.
CPC .......... *A61B 5/14551* (2013.01); *A61B 5/413* (2013.01)

(58) Field of Classification Search
CPC ............................. A61B 5/14551; A61B 5/413
USPC ................. 600/309–310, 317, 322–327, 349
See application file for complete search history.

(56) References Cited

U.S. PATENT DOCUMENTS

| | | | | |
|---|---|---|---|---|
| 4,419,999 A | * | 12/1983 | May et al. | 600/504 |
| 4,437,475 A | * | 3/1984 | White | 607/126 |
| 4,658,825 A | * | 4/1987 | Hochberg et al. | 600/313 |
| 5,237,994 A | * | 8/1993 | Goldberger | 600/323 |
| 5,298,742 A | * | 3/1994 | Friauf et al. | 250/239 |
| 5,599,317 A | * | 2/1997 | Hauser | 604/256 |
| 6,473,654 B1 | * | 10/2002 | Chinn | A61N 1/05 600/375 |
| 6,487,343 B1 | * | 11/2002 | Lewandowski et al. | 385/51 |
| 6,587,701 B1 | | 7/2003 | Stranc et al. | |
| 6,587,703 B2 | * | 7/2003 | Cheng et al. | 600/310 |
| 7,355,688 B2 | | 4/2008 | Lash et al. | |
| 7,525,647 B2 | | 4/2009 | Lash et al. | |
| 7,790,945 B1 | * | 9/2010 | Watson, Jr. | 602/43 |
| 2002/0161290 A1 | * | 10/2002 | Chance | A61B 5/14551 600/323 |
| 2004/0230118 A1 | * | 11/2004 | Necola Shehada | A61B 5/0031 600/441 |
| 2006/0149145 A1 | * | 7/2006 | Furnary et al. | 600/325 |
| 2007/0051379 A1 | * | 3/2007 | Lash et al. | 128/898 |
| 2007/0055119 A1 | * | 3/2007 | Lash | G01N 21/3151 600/323 |
| 2008/0106792 A1 | * | 5/2008 | Lash et al. | 359/618 |
| 2008/0154102 A1 | * | 6/2008 | Frangioni et al. | 600/317 |
| 2008/0316488 A1 | * | 12/2008 | Mao | A61B 5/14552 356/432 |

(Continued)

OTHER PUBLICATIONS

Sposato et al., "Ambulant Vacuum-Assisted Closure of skin-graft dressing in the lower limbs using a portable mini-VAC device", British J. Plastic Surgery (2001), 54, pp. 235-237.

(Continued)

*Primary Examiner* — Rene T Towa
(74) *Attorney, Agent, or Firm* — Aka Chan LLP

(57) ABSTRACT

A sensor probe has a sensor unit which is embedded in a sheath member which is suturable. The sheath member allows the sensor unit to be sutured and secured to any tissue even in a wet or moist environment. The sensor probe in accordance with the present invention is particularly useful as an intraoral sensor probe for measuring oxygen saturation of a flap tissue inside the oral cavity.

42 Claims, 13 Drawing Sheets

(56) References Cited

U.S. PATENT DOCUMENTS

2009/0287197 A1\* 11/2009 Hanley .................. A61B 18/24
                                                                606/15
2010/0020165 A1\* 1/2010 Crucs ..................... A61B 6/145
                                                                348/77

OTHER PUBLICATIONS

Kamolz, L.P. et al., "Continuous Free-Flap Monitoring with Tissue-Oxygen Measurements: Three-Year Experience," Journal of Reconstructive Microsurgery, vol. 18, No. 6, Aug. 2002, pp. 488-491.
Thorniley, M.S., et al., "The Use of Near-Infrared Spectroscopy for Assessing Flap Viability During Reconstructive Surgery," British Journal of Plastic Surgery, vol. 51, 1998, pp. 218-226.
The Vacuum Assisted Closure brochure—"Advanced Dressings—Dedicated Dressings for Specific Wound Applications", KCI, www.woundvac.com, 2005, 6 pages.

\* cited by examiner

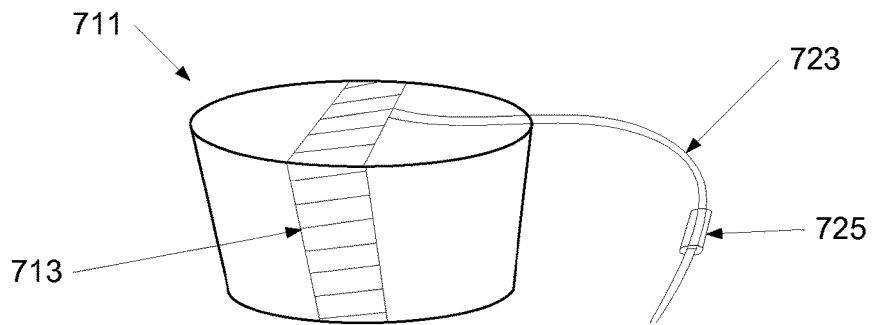
Figure 7A
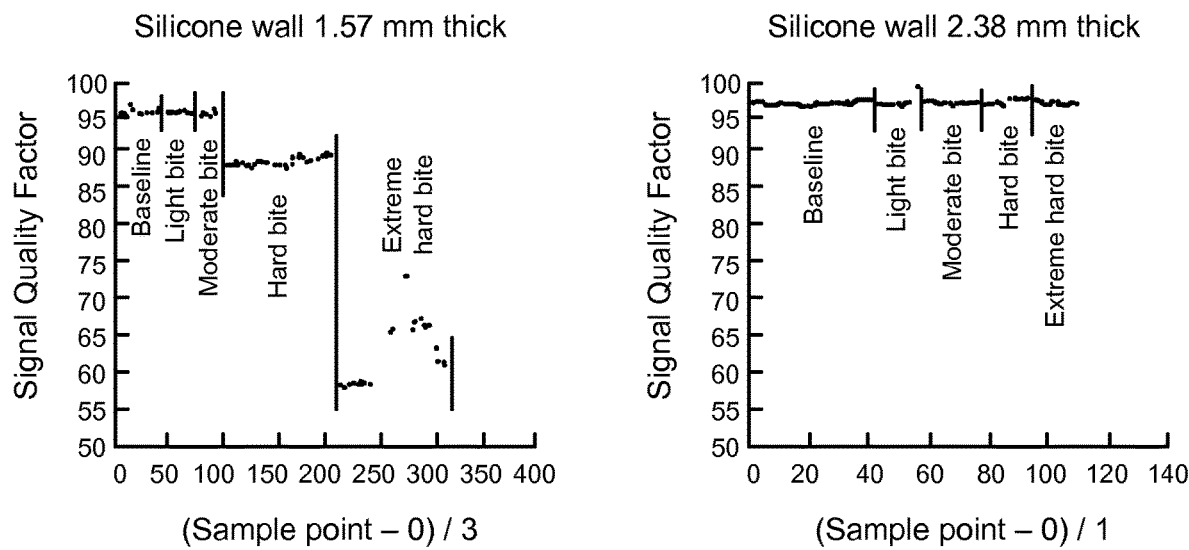
Figure 7B
Figure 7C

PROBE FOR MONITORING WET OR MOIST ENVIRONMENTS

CROSS-REFERENCE TO RELATED APPLICATIONS

This application is a continuation-in-part of U.S. design patent application Ser. No. 29/336,797, filed May 8, 2009, which is incorporated by reference along with all other references cited in this application.

BACKGROUND OF THE INVENTION

The invention relates to the field of medical devices and more specifically to oximeters and other medical sensor probes.

Oral and pharyngeal cancer is one of the ten most common cancers worldwide. More than 34,000 Americans are diagnosed with oral and pharyngeal cancer per year. Over ninety percent of cancers of the mouth are squamous cell carcinomas arising from mucosal surface epithelium. Sometimes these cancers involve soft tissue in the oral cavity as well as hard tissue such as jaw bone. Treatment of oral and pharyngeal cancer typically includes excision of an affected tissue, which can damage cosmetic or function of the oral cavity. For example, speech or mastication function of a patient may become impaired due to excision of affected oral tissue.

After excision of diseased tissue, the defects of the oral cavity can be approached in a number of different ways. Small defects of the oral cavity can be excised and closed by suturing. More extensive defects can be repaired or reconstructed with skin grafts, or other tissue flaps. A graft is a procedure performed where healthy skin (or mucosal tissue) is removed from a donor site of the body and transplanted to a recipient site. A flap is similar to a graft in that a transplantation of tissue occurs. The main difference between the two is that a flap is transferred with its blood supply intact, and a graft is a transfer of tissue without its own blood supply. Therefore, survival or the graft depends entirely on the blood supply from the recipient site.

The blood flow through a transplanted flap or graft may change over time after a transplant is completed. For example, a transplanted flap may sometimes die when the blood flow through the transplanted tissue is compromised. A blood clot or a pinched vein in the transplanted tissue may cause the transplanted tissue to die. It is often difficult to tell whether the transplanted tissue is healthy or damaged until it is too late (e.g., when the transplanted tissue color changes due to hypoxia).

There are medical devices that can assess blood supply or oxygenation state of a tissue. For example, oximeters are noninvasive medical devices that can be used to measure tissue oxygen saturation. Human tissues include a variety of light-absorbing and light-scattering chromophores (e.g., deoxygenation and oxygenated hemoglobins) which can interact with electromagnetic waves transmitted thereto and traveling therethrough. Light-absorption and light-scattering patterns differ significantly between deoxygenated and oxygenated hemoglobins at certain wavelengths of light. An oximeter uses this difference to determine oxygen saturation of tissues.

While oximeters are sensitive and reliable in measuring tissue oxygen saturation, there is no oximeter sensor probe suitable for use inside the oral cavity. The sensor probes that are available cannot be applied and held steady on a flap or other tissue inside the oral cavity for a prolonged period. For instance, a sensor probe can get dislodged easily by saliva or by movement of a tongue. Assessing the oxygenation state of a transplanted flap before, during, and after a reconstruction surgery is important as it is an indicator of whether the transplanted flap is receiving sufficient blood supply and oxygen.

Accordingly, there is a need to improve oximeter sensor probes and other medical devices for determining blood supply or oxygenation state of a tissue inside the oral cavity. The present invention addresses these and other needs.

BRIEF SUMMARY OF THE INVENTION

The present invention relates to assessing the viability of tissue such as a transplanted flap tissue inside the oral cavity or in other areas of the body. According to one aspect of the present invention, a sensor probe has a sensor unit and a sheath member with a recessed region for embedding and surrounding the sensor unit. The sensor probe also has a cable which operatively connects the sensor unit to a system unit (e.g., a monitoring console).

The sheath member has a lip region surrounding a scanning surface of the sensor unit. The lip region of the sheath member can be sutured on a tissue inside the oral cavity, securing the sensor unit stably so that oxygen saturation or other optical measurements can be made during surgery or recovery. The sheath member can also provide cushioning effect so that hard edges of the sensor unit do not add uneven pressure points on the tissue.

In one embodiment, the lip region of the sheath member is suturable. The sheath member can be a solid elastomeric material which can be pierced by a surgical needle. In a specific implementation, the sheath member is comprised of a silicone material. In some embodiments, the sheath member can be transparent or translucent so that it is easier for a surgeon to suture the sheath member on a tissue. In an implementation, the lip region of the sheath member has a width between about 2 millimeters and about 5 millimeters.

In another embodiment, the sensor unit is an intraoral sensor probe which is used inside the oral cavity. A tissue being monitored by the intraoral sensor probe can be a flap tissue covering a defect in the oral cavity.

In another embodiment, the sensor probe has one or more optical fibers where distal ends of the optical fibers are connected to source and detector structures of the sensor unit.

In another embodiment, a portion of the sensor probe cable is flattened so that it can lay relatively flat over a tissue and does not roll on top of a tissue.

In another embodiment, the sensor probe has a first tubing sleeve covering a portion of the cable proximate to the sensor unit. The first tubing sleeve can be used as a secondary suture point. In yet another embodiment, the sensor probe has a second tubing sleeve covering a portion of the cable proximate to the first tubing sleeve to provide an additional protection against cable damage due to accidental biting of the cable by a patient. The first tubing sleeve, the second tubing sleeve, or both sleeves can be made of a silicone material.

In another embodiment, the sensor unit further includes a second source structure and a second detector structure. A first distance is between the first source structure and the first detector structure. A second distance is between the first source structure and the second detector structure. A third distance is between the second source structure and the first detector structure. A fourth distance is between the second source structure and the second detector structure. In this embodiment, the first distance is not equal to the fourth distance, and the second distance is not equal to the third distance.

In another embodiment, the sensor unit further comprises a third detector structure and a fourth detector structure which are located between the first detector structure and the second detector structure, where all of the detector structures are linearly aligned with respect to one another. In an embodiment, a distance between the first detector structure and the second detector structure is 5 millimeters; a distance between adjacently located detector structures is 5/3 millimeters; and a distance between the first detector structure and the first source structure is 5 millimeters.

According to another aspect of the present invention, a method for determining an oxygen saturation value for a tissue includes contacting a scanning surface of a sensor probe on a tissue. Then the sensor probe is secured on the tissue by piercing and suturing the lip region of the sheath member to the tissue with a suturing needle. A first light is transmitted through the first source structure into the tissue, and a second light is received through the tissue at the detector structure. An oxygen saturation value for the tissue can be determined based on values for the first and second light.

In one embodiment, the sensor probe is an intraoral sensor probe, and the tissue is a flap tissue inside the oral cavity. In another embodiment, the sensor probe further includes a first tubing sleeve covering a portion of the cable nearby the sensor unit, where the first tubing sleeve is sutured to the flap tissue or to a tissue adjacent to the flap tissue.

According to yet another aspect of the present invention, a method for determining an oxygen saturation value of a tissue includes contacting a scanning surface of a sensor unit on a tissue of a patient. Then a sponge dressing is applied over the tissue. A vacuum plate and an adhesive drape are applied over the sensor unit and the sponge dressing. An oxygen saturation value for the tissue can be determined by using the sensor probe. In one embodiment, the tissue is a wound bed, a graft tissue, or a flap tissue. In another embodiment, the tissue can be a fenestrated skin graft, a muscle flap tissue, a cutaneous flap tissue, or a myocutaneous flap tissue.

According to yet another aspect of the present invention, a system includes a sensor probe comprising a sensor unit embedded in a sheath member and a cable, and a system unit, wherein the sensor probe and the system unit are operatively connected by the cable.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 7A shows a sensor probe with its scanning surface contacting a phantom which mimics a human tissue, where a portion of the sensor probe cable is covered with a silicon tubing sleeve.

FIG. 7B shows the effects of human biting on the silicon tubing sleeve which has a wall thickness of 1.57 millimeters.

FIG. 7C shows the effects of human biting on the silicon tubing sleeve which has a wall thickness of 2.38 millimeters.

DETAILED DESCRIPTION OF THE INVENTION

Figure 1:
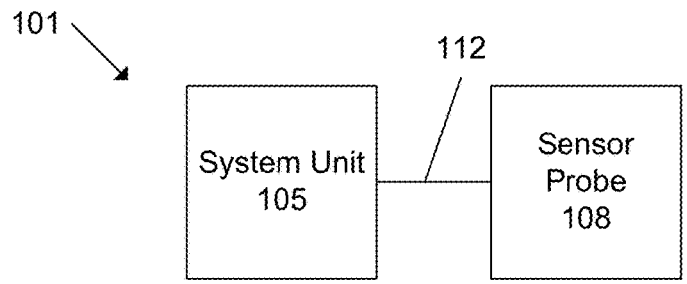
FIG. 1 shows a block diagram of an oximeter system for measuring oxygen saturation of tissue in a patient.

Assessing the blood supply to a transplanted tissue, such flap or graft tissue, is important as it is a key indicator of viability of the transplanted tissue. Monitoring the blood flow to and oxygen saturation of a transplanted tissue inside the oral or nasopharyngeal cavity can be particularly challenging because of its wet or moist environment and involuntary movement of soft tissues, such as tongue. While a number of sensor probes are currently available to make optical measurements, such as oxygen saturation, they are not suitable for applying to a transplanted flap tissue inside the oral or nasopharyngeal cavity.

A sensor probe in accordance with the present invention provides features which allow a sensor unit (i.e., a sensor head with a scanning surface which emits light to a tissue and receives reflected light from the tissue) to be secured on a flap or graft tissue inside the oral or nasopharyngeal cavity. For instance, the sensor probe has a sensor unit and a sheath member which has a recessed region on which the sensor unit rests. The sheath member has a lip region surrounding the scanning surface of the sensor unit.

In embodiments of the invention, the sheath member is suturable because it is soft or elastomeric or both. Thus, the lip region of the sheath member surrounding the sensor unit can be pierced with a surgical needle and can be sutured to a flap tissue. As a result, the sensor unit assembly (i.e., a sensor unit surrounded by a sheath member) can be secured to a location of interest for a prolonged period of time without being disturbed during surgery or recovery. Thus, the sensor probe in accordance with the present invention can be used inside the oral or nasopharyngeal cavity.

The sensor probe in accordance with the present invention has applications other than making optical measurements in the oral or nasopharyngeal cavity. For example, the sensor probe can be used to monitor a skin graft over a wound. In instances where a transplanted tissue is too fragile to be sutured, such as skin grafts, other methods can be used to secure the sensor unit to a transplanted tissue. For example, a negative vacuum pressure can be applied instead of suturing to secure a sensor unit or sensor unit assembly over a transplanted tissue while the wound heals and new vasculatures are formed.

In one implementation of the invention, the sensor probe has an oximeter sensor unit which measures oxygen saturation of the transplanted tissue, which is an indicator of sufficiency of the blood supply to the tissue. The oxygen saturation measurements of a transplanted tissue can be made at various time points. For example, oxygen saturation measurements can be made from the tissue when it is intact at the donor site, as well as when it is elevated from the donor site or at the recipient site after the reconstruction surgery. A sensor probe can provide an accurate and reliable way to assess the oxygenation state of a transplanted tissue during the process of a reconstruction surgery.

Embodiments of the invention provide for a number of advantages. The sensor probes in accordance with the present invention allow a doctor to monitor the blood flow or oxygenation state of flap or graft tissue in a wet or moist environment. Since the flap or graft tissues can be monitored during surgery and recovery, it provides an opportunity for the doctor can take an immediate remedial measure if the sensor probe determines that the condition of a transplanted tissue is deteriorating or is not optimal. The doctor need not wait until the end of a recovery period to determine if a transplant surgery was successful.

Furthermore, a sheath member of the present sensor probe provides mechanical stability and cushioning effects. The lip region of the sheath member surrounding a sensor unit lengthens and widens a contact surface for the sensor unit and assures more stable planar contact of the scanning surface of the sensor unit with a target tissue. The sheath member also covers corners and edges of a sensor unit, which is typically made of a hard material such as metal. Softness or elasticity of the sheath member helps to protect delicate tissues from any hard and sharp corners of the sensor unit. Also, the sheath member assists in evenly distributing contact pressure associated with corners and edges of the sensor unit on the tissue.

Examples of embodiments of the invention are illustrated using figures and are described below. The figures described herein are used to illustrate embodiments of the invention, and are not in any way intended to be restrictive of the broad invention. Embodiments of the invention are not limited to the specific arrangements and constructions shown and described. For example, features shown in one figure can be combined with features shown in another figure.

FIG. 1 shows an oximeter system 101 for measuring oxygen saturation of a tissue in a patient. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers), or any combination of these or other types of connections. In other implementations of the invention, however, connection 112 may be wireless such as via a radio frequency (RF) or infrared communication.

Typically, the system is used by placing the sensor probe in contact or close proximity to tissue (e.g., skin, flap tissue, or graft tissue) at a site where oxygen saturation or other related measurement is desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines the oxygen saturation of the tissue and displays a value on a display of the system unit.

In an implementation, the system is a tissue oximeter, which can measure oxygen saturation without requiring a pulse or heart beat. A tissue oximeter of the invention is applicable to many areas of medicine and surgery including plastic surgery and spinal surgery. The tissue oximeter can make oxygen saturation measurements of tissue where there is no pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, 7,247,142, 7,355,688, and 7,525,647. These patents are assigned to the same assignee as this patent application and are incorporated by reference.

Figure 2:
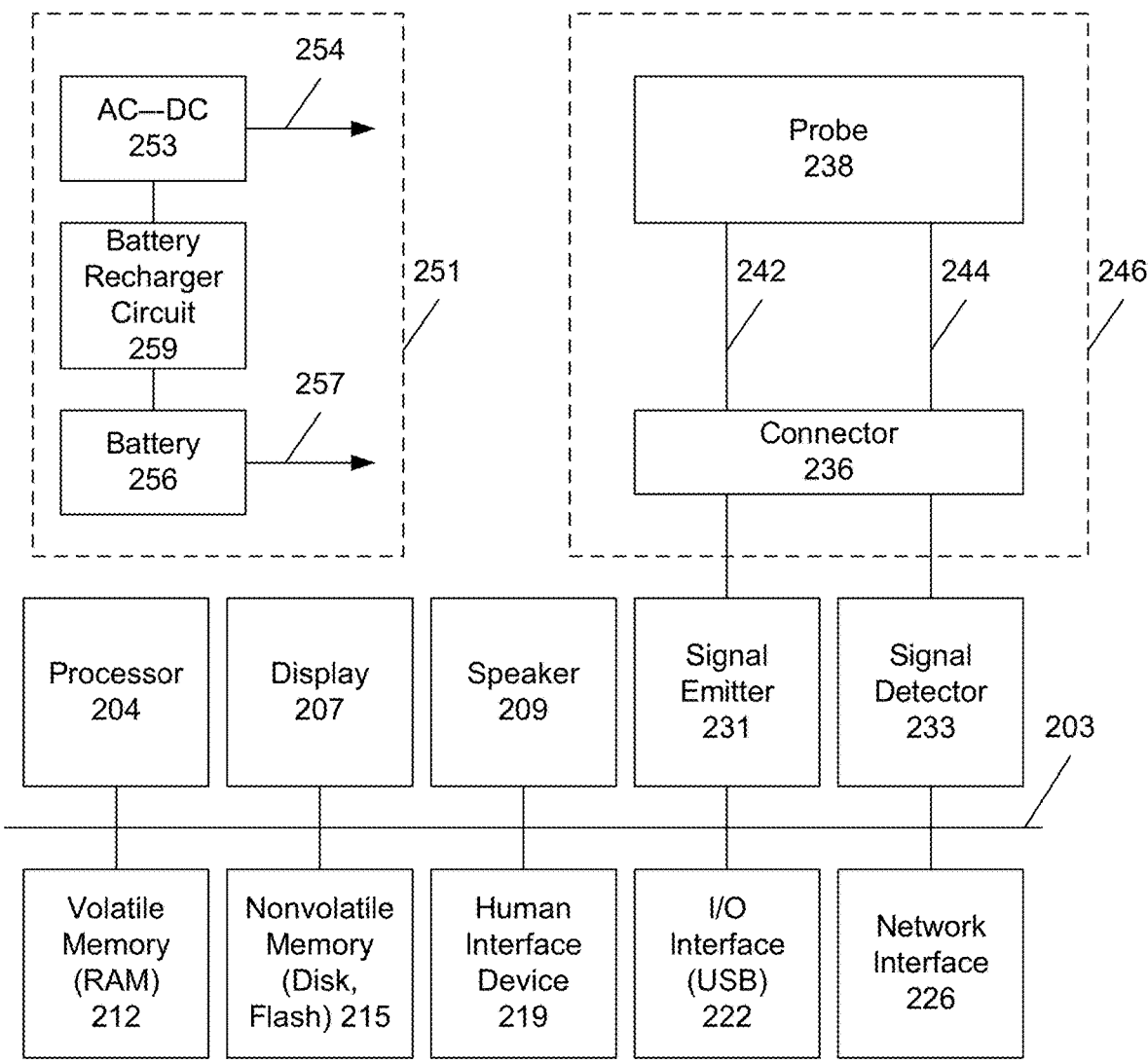
FIG. 2 shows a more detailed block diagram of a specific implementation of the system of FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system.

Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires.

Signal emitter 231 is a light source that emits light at one or more specific wavelengths. In a specific implementation, two wavelengths of light (e.g., 690 nanometers and 830 nanometers) are used. In other implementations, other wavelengths of light may be used. The signal emitter is typically implemented using a laser diode or light emitting diode (LED). Signal detector 233 is typically a photodetector capable of detecting the light at the wavelengths produced by the signal emitter.

Connector 236 may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. When a probe is inserted, the system uses the second keying feature to determine which type of probe is connected to the system. Then the system can perform the appropriate functions, use the proper algorithms, or otherwise make adjustments in its operation for the specific probe type.

In various implementations, the system is powered using a wall outlet or battery powered, or both. Block 251 shows a power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected to the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www-.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3:
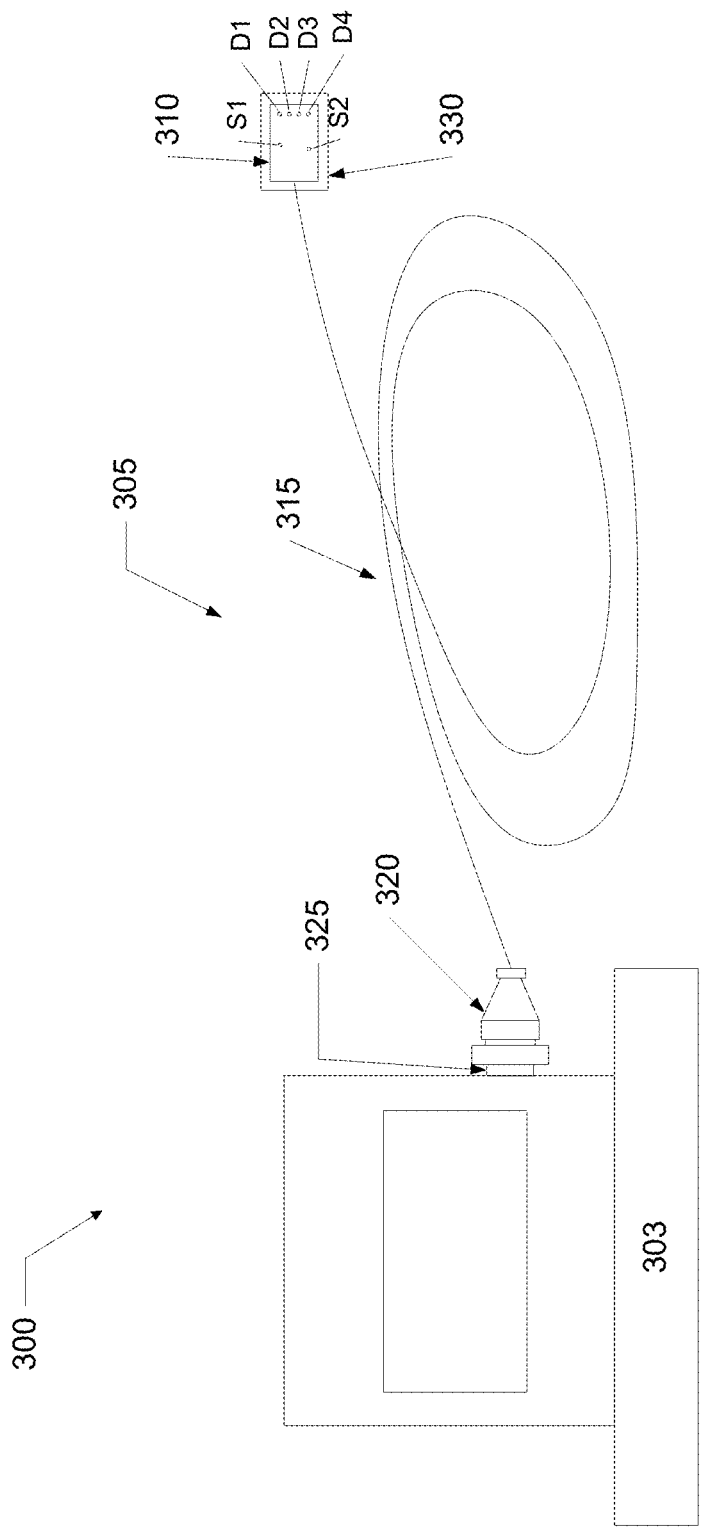
FIG. 3 shows a system of the invention including a monitoring console, a sensor unit assembly, and a cable connecting the sensor unit assembly to the monitoring console.

FIG. 3 shows one implementation of a system 300 which includes a console 303 (e.g., system unit) and a sensor probe 305. The sensor probe includes a sensor unit 310 (sometimes referred to as a sensor head) and a sheath member 330 embedding and surrounding the sensor unit. The sensor probe also includes a cable 315 where one end of the cable is operatively connected to the sensor unit and the other end includes a connector 320. The connector of the sensor probe can be removably attached to a receptacle 325 on the console. Therefore, the cable operatively connects the sensor unit to the console which, among other things, controls and displays optical measurements.

As shown in FIG. 3, sheath member 330 surrounds and holds the sensor unit in place, with its scanning surface exposed, allowing the sensor unit to contact and make optical measurements. The sheath member is made of a soft or elastomeric material or has features which allow the sheath member to be sutured to a tissue. This feature is particularly useful when optical measurements are desired in a wet or moist environment of the body, such as the oral cavity. Furthermore, the sensor unit surrounded by the sheath member (referred to as a sensor unit assembly) can be secured to a tissue by applying vacuum when the tissue is too delicate to be sutured. The sensor unit assembly will be described more detail below with respect to FIGS. 4A through 4G.

Sensor unit 310 makes optical measurements of biological state of a target tissue, such as blood flow or oxygen saturation. In an implementation, sensor unit 310 can be an oximeter sensor unit which measures oxygen saturation of a tissue. An oximeter sensor unit includes at least one source structure and one detector structure.

In this application, a source structure refers to a structure in the scanning surface of the sensor unit that provides light to be transmitted into a target tissue. The source structure can generate light, or it can be a structural component that transmits light generated elsewhere (e.g., from an upstream source.) A detector structure refers to a structure in the oximeter sensor unit that detects light (or that is a structural component of the detection process) which is scattered and reflected from the tissue.

In the implementation shown in FIG. 3, oximeter sensor unit 310 includes two source structures (S1 and S2) and four detector structures (D1, D2, D3, and D4) on its scanning surface that contacts a target tissue. The source structures and detector structures are shown as openings in oximeter sensor unit 310, and they may be referred to as openings or sensor openings in this application. The source structures and detector structures are physically and functionally connected to console 303 by conductors (e.g., optical fibers, electrical wires, or both) which run from the sensor unit to connector 320 inside the cable. The connector of the sensor probe aligns and couples the conductors with their counterparts in the receptacle of the console.

In one embodiment, a source structure can be a laser or light emitting diode (LED) that emits a light of a specific wavelength suitable to monitor oxygen saturation. A detector structure can be a photodiode (e.g., a PN diode, a PIN diode, or an avalanche diode) that detects the light transmitted and reflected from a tissue, after the source structure emits the light into the tissue. In an oximeter sensor unit, both LEDs and photodiodes are located at the scanning surface of the sensor unit. These LEDs and photodiodes can then be electrically connected to a system unit or console. In this embodiment, since the light is generated next to the tissue surface and subsequently detected at the tissue surface, there is less attenuation of a signal.

In another embodiment, a source structure is an opening in an oximeter sensor unit (at its scanning surface) with an optical fiber inside, which is connected to an emitter located elsewhere (e.g., system unit). Likewise, a detector structure is an opening in an oximeter sensor unit (at its scanning surface) with an optical fiber inside, which is connected to a detector located elsewhere. The optical fibers from each oximeter sensor unit are then connected to either an emitter or a detector which may be located in a system unit or console.

In the latter embodiment, one or more optical fibers can run along the length of the cable, and distal ends of the optical fibers (or fiber optic bundle) is inserted or attached to sensor openings. The proximal ends of the optical fibers terminate inside connector 320. The proximal ends of the optical fibers in the connector are aligned with their corresponding optical fibers in the receptacle of the console, so that light generated in the console can be delivered to the oximeter sensor unit of a sensor probe.

While FIG. 3 illustrates an embodiment with six sensor openings in the oximeter sensor unit, any suitable number of sensor openings can be present in the sensor probe. For example, there may be one, two, three, four, five, six, seven, or eight or more sensor openings. Any one or more sensor openings can be source structures, and any one or more sensor openings can be detector structures. A number of source structures can be equal to a number of detector structures in the oximeter sensor unit, or they can be different.

Further, oximeter sensor unit 310 shown in FIG. 3 has a particular sensor opening pattern where the arrangement of source structures and detector structures are asymmetrical. The detector structures are aligned in a linear row and source structures are offset from each other. In other words, a line drawn through the detector structures is not parallel to a line drawn through the source structures. Additionally, the distance between openings D1 and D4 is shorter than the distance between openings S1 and S2.

The selection of a number of sensor openings or sensor opening pattern for a sensor unit depends on many factors. For example, a small number of sensor openings would require a relatively small scanning surface and thus a small sensor unit can be produced. A large number of sensor openings may increase sensitivity of optical measurements. Furthermore, a larger separation between a source structure and a detector structure may allow the detector structure to detect light after the light has penetrated deeper into the tissue, compare to a sensor unit with a smaller separation between the two structures. Variations of sensor openings patterns are further discussed below with respect to FIGS. 8A through 8H.

As shown in FIG. 3, cable 315 operatively couples sensor unit 310 and console 303 electrically or optically, or both. In one implementation, the cable includes one or more optical wave guides (e.g., multiple strands of fiber optic cable) enclosed in a flexible cable jacket, such as PVC jacket. The optical wave guides may be used to transmit light from the console, through the oximeter sensor unit and out openings in the oximeter sensor unit and into the tissue. The optical wave guides may also be used to transmit the light received from the tissue back to the console.

In another implementation, when radiation sources such as light emitting diodes (LEDs) and photodiodes are placed in the sensor unit, the cable may contain electrical wiring to transmit power to the radiation sources and photodiodes. In some implementations, the cable may contain both optical fibers and electrical wires.

In an embodiment of the invention, each opening on the sensor unit and corresponding cable is dedicated to a particular purpose. For example, a first opening on the sensor unit (and corresponding fiber optic cable) is dedicated to transmitting light from the console. A second opening on the sensor unit is dedicated to transmitting a signal received at the second opening to the console. In other embodiments, a particular opening and cable are used for multiple purposes (e.g., both input and output) using a scheme such as multiplexing.

In a specific implementation, the cable is passive. For example, it will not contain any active, generative properties to maintain signal integrity. However, in other implementations, the cable may include active components. The cable may include active components to amplify the signal transmitted through the sensor unit, received at the sensor unit, or both. For example, long lengths of cable subject to significant attenuation may require amplification. Amplification may also be required if the monitored site contains a particularly dense structure such as bone.

In embodiments of the invention, the length of the cable may vary. In a specific implementation, the length of the cable ranges from about 1.2 meters to about 3 meters. For example, the cable may be about 1.3, 1.4, 1.5, 1.6, 1.7, 1.8, 1.9, 2, 2.1, 2.2, 2.3, 2.4, 2.5, 2.6, 2.7, 2.8, 2.9, or 3.0 meters long or greater. Depending on the specific application, the cable length may be less than 1.2 meters. In some applications, the cable length will be greater than 3 meters. It may be desirable to use longer cables when a patient is immune compromised and needs to be kept away from sources of contamination, such as a console.

Connector 320 at the end of the cable attaches the sensor probe to its receptacle on the console. The connector also protects the cable from accidental disconnection. The connector may include a collar that threads onto the receptacle on the console. Alternatively, the connector may include a lug closure, press-fit, or snap-fit components.

In a specific implementation, there may be other connectors on the cable besides connector 320 and receptacle 325. These other connectors allow the cable to be separated into two or more pieces, allowing additional lengths of cable to be attached, or both. Additional connectors allow the overall length of the cable to be adjusted as necessary. Furthermore, only a portion of the cable that is contaminated can be disconnected and disposed, rather than disposing the entire length of the cable after each use.

In one implementation, console 303 (sometimes referred to as a monitoring console or system unit) shown in FIG. 3 can be a portable console which may be hand carried. A portable console can follow a patient and optical measurements can be made anywhere in the hospital. In this implementation, it is desirable that the portable console is battery operated. In another implementation, the console may be a large, nonportable device that is attached to a wall or secured to a stand. In this implementation, the system is typically connected to AC power.

The console may include a mass storage device to store data. Mass storage devices may include mass disk drives, floppy disks, magnetic disks, fixed disks, hard disks, CD-ROM and CD-RW drives, DVD-ROM and DVD-RW drives, flash and other nonvolatile solid-state storage drives, tape storage, reader, and other similar devices, and combinations of these.

The stored data may include patient information. This includes, for example, the patient's name, social security number, or other identifying information, oxygen saturation measurements and the time and date measured. The oxygen saturation measurements may include high, low, and average values and elapsed time between measurements.

The above drives may also be used to update software in the console. The console may receive software updates via a communication network such as the Internet.

In an implementation, the console also includes an interface for transferring data to another device such as a computer. The interface may be a serial, parallel, universal serial bus (USB) port, RS-232 port, printer port, and the like. The interface may also be adapted for wireless transfer and download, such as an infrared port. The system transfers data without interruption in the monitoring of the patient.

The console also includes a display screen which may display the patient's data, such as an oxygen saturation measurement. The screen may be a flat panel display or include a touch screen interface so that the user can input data into the console.

The console, in addition to the display, may also include a processor, signal emitter circuit, signal detector circuit, and a receptacle to removably couple ends of one or more conductors. In a specific implementation, the ends of one or more conductors (e.g., optical fibers or electrical wires) are instead permanently connected to the console. The signal emitter circuit may operate to send a signal through the one or more conductors. The signal detector circuit then receives a signal via one or more conductors.

In a specific implementation, the signal emitter circuit may include one or more laser emitters, light emitting diode (LED) emitters, or both. The signal emitter circuit may be used to generate an optical signal having two or more different wavelengths to be transmitted through the sensor unit. The wavelengths may range from about 600 nanometers to about 900 nanometers.

In a specific implementation, the console includes a first radiation source and a second radiation source. The radiation sources may be dual wavelength light sources. In other words, first radiation source provides two wavelengths of radiation and second radiation source provides two wavelengths of radiation. First radiation source, second radiation source, or both may include one or more laser diodes or light emitting diodes (LEDs) that produce light in any wavelength, but typically the wavelengths range from about 600 nanometers to about 900 nanometers. In a specific implementation, a first wavelength of light is generated that has a wavelength of about 690 nanometers. A second wavelength of light is generated that has a wavelength of about 830 nanometers.

In a specific implementation, one or more near-infrared radiation sources are included within the console. In other implementations, the radiation sources may be external to the console. For example, the radiation sources may be contained within a separate unit between the console and sensor probe. The radiation sources may, for example, be contained in an oximeter sensor unit itself or in other parts (e.g., in the console). In yet another implementation, some radiation sources may be within the console while other radiation sources are external to the console.

These radiation sources may be near-infrared lasers. In a specific implementation, there is one near-infrared laser located within the console. In other implementations, there may be more than one near-infrared laser. For example, there may be 2, 3, 4, 5, 6, 7, 8, 9, or 10, or more than 10 radiation sources. In another implementation, the radiation sources may include those that produce a visible light.

In one implementation, light emitted by different radiation sources is provided to a beam combiner via optical fibers. The beam combiner effectively merges the light from different radiation sources, and the merged light is then provided via output optical fibers. The output fibers are arranged to allow the merged or combined light to be homogenized to ensure that the light is substantially uniformly distributed across the output fibers when the light enters the sensor unit. The beam combiner may be located in the console, or may be located outside of the console.

In a specific implementation, a single pulse of light is transmitted into the tissue. In another implementation, multiple pulses of light may be transmitted into the tissue. For example, a first pulse of light may be received by a first detector. A second pulse of light may be received by a second detector.

When light is transmitted to a target tissue via source structures in the sensor unit, light scatters due to heterogeneous structure of the tissue, and some of the light is absorbed by chromophores such as hemoglobin. An attenuated version of the light that is reflected by the tissue is detected by detector structures in the sensor unit and is transmitted to the console. The oxygen saturation or hemoglobin concentration of the tissue can be calculated based on a value of the initial light generated by the signal emitter and a value of an attenuated version of the light that is reflected from the tissue and is subsequently detected by the signal detector.

In a specific implementation, an attenuation ratio is used to determine tissue oxygen saturation level or value ($StO_2$), hemoglobin concentration (Hgb), or both. The term oxygen saturation level (or value) refers to the percentage of hemoglobin that is bound to oxygen at the time of measurement. Additional details on attenuation methods are also discussed in U.S. patent application Ser. No. 12/126,860, filed May 24, 2008, which is incorporated by reference. The attenuation ratio method may also include techniques discussed in U.S. Pat. No. 6,587,701, which is incorporated by reference.

In the automatic error-cancellation or self-calibration scheme, the system factors such as source intensity, detector gain, and loss of light in the optical fibers and connectors are cancelled automatically. The automatic error-cancellation scheme is discussed in more detail as equations 5a and 5b in U.S. Pat. No. 6,597,931, which is incorporated by reference. The self-calibration scheme may also include equations discussed in U.S. Pat. Nos. 6,516,209, 6,735,458, and 6,078,833, U.S. patent application Ser. No. 12/126,860, filed May 24, 2008, and New Optical Probe Designs for Absolute (Self-Calibrating) NIR Tissue Hemoglobin Measurements, Proc. SPIE 3597, pages 618-631 (1999), which are incorporated by reference.

Figure 4A:
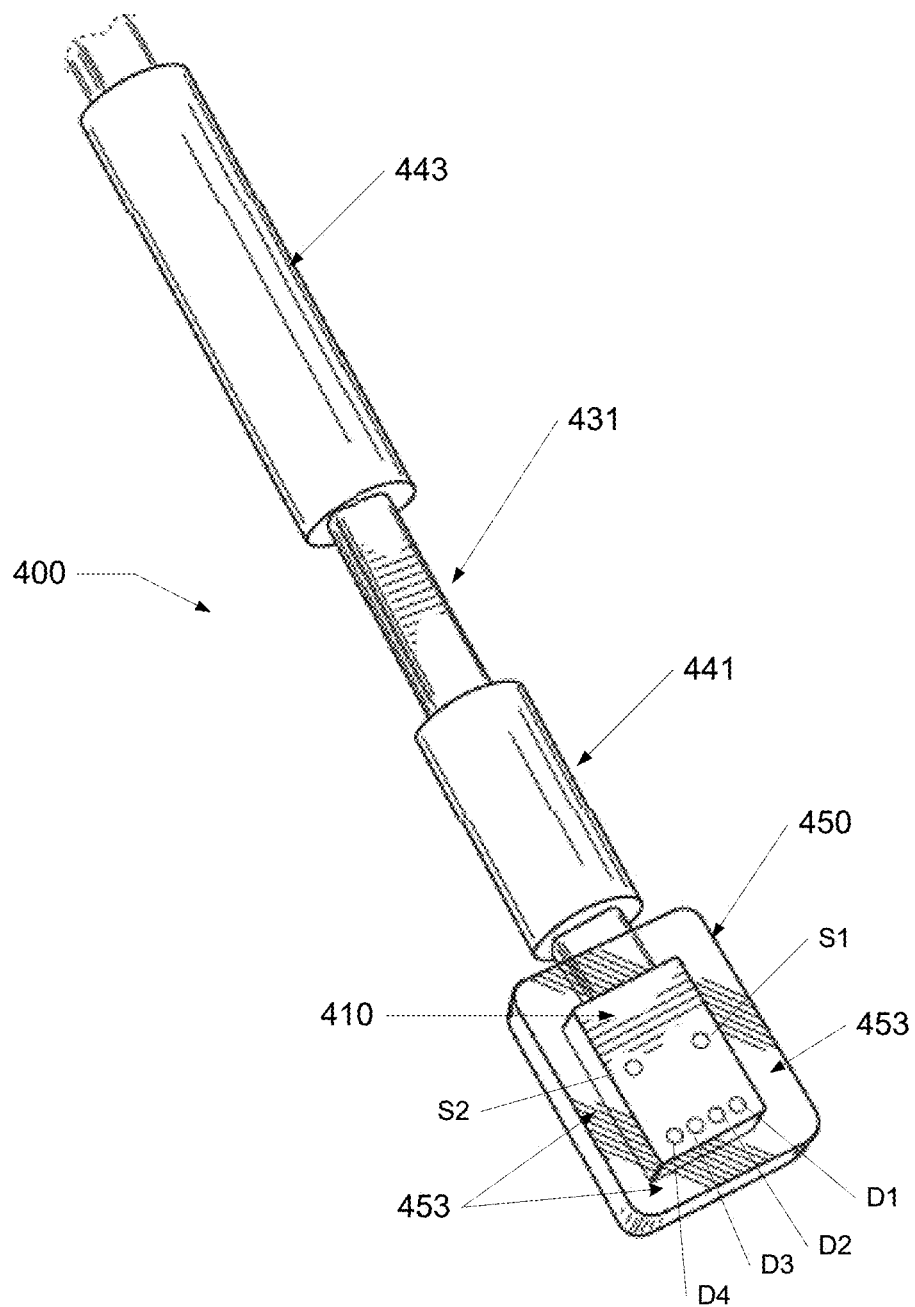
FIG. 4A shows a perspective view of a sensor probe where a sensor unit is embedded in a sheath member, and its cable is covered by two separate tubing sleeves.

FIG. 4A shows a perspective view of one implementation of a sensor probe 400. The sensor probe has a sensor unit 410 which is embedded and surrounded by a sheath member 450, except a scanning surface of the sensor unit which is exposed for contact. The sheath member has a lip region 453 which surrounds the scanning surface of the sensor unit. The lip region can provide a cushioning effect for a tissue which is contacted by the sensor unit, as well as providing a region that can be pierced by a surgical needle to suture the sensor unit assembly to a tissue.

The scanning surface of the sensor unit is a surface or face of the sensor unit which has source structures to transmit light to a tissue and detector structures to receive reflected light from the tissue to make optical measurements. The scanning surface of sensor unit 410 has source structures S1 and S2 and detector structures D1, D2, D3, and D4.

A cable 431 is connected to the sensor unit, through a slot 457 (shown in FIG. 4G) on a bottom wall of the sheath member. A portion of the cable proximate to the sensor unit is covered by a first tubing sleeve 441. Another portion of the cable proximate to the first tubing is covered by a second tubing sleeve 443. The properties and functions of the first and second tubing sleeves are described more detail below.

Figure 4B:
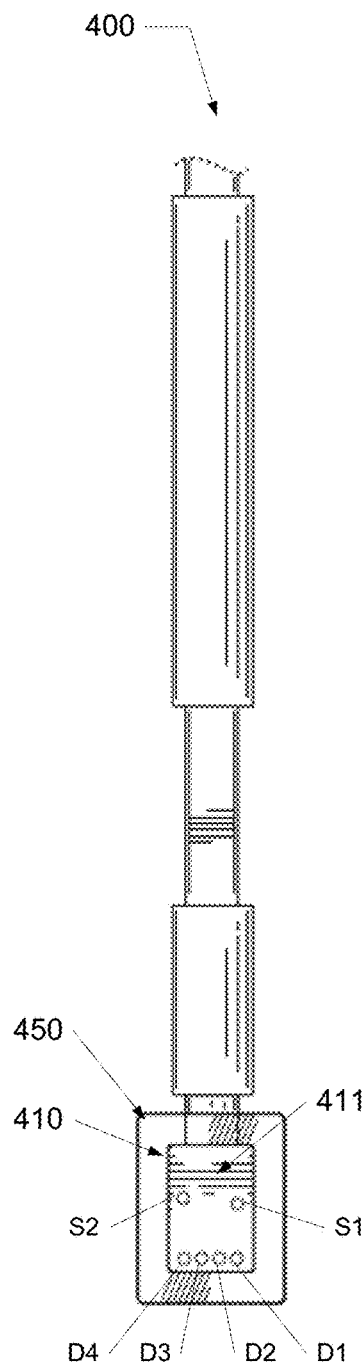
FIG. 4B shows a front view of the sensor probe shown in FIG. 4A.

FIG. 4B shows a front view of the sensor probe shown in FIG. 4A. A scanning surface 411 of the sensor unit is exposed to air, whereas the rest of the sensor unit is embedded in sheath member 450. The scanning surface of the sensor unit has two source structures in an offset or asymmetric orientation with respect to detector structures which are linearly aligned with respect to one another. In other words, a line drawn through the detector structures are not parallel to a line drawing through the source structures. Embodiments of the invention are not limited to the particular arrangement of source structures and detector structures shown in FIGS. 4A and 4B, and include other asymmetric or symmetric arrangements. Other examples of source and detector structure arrangements are discussed below with respect to FIGS. 8A through 8H.

Figure 4C:
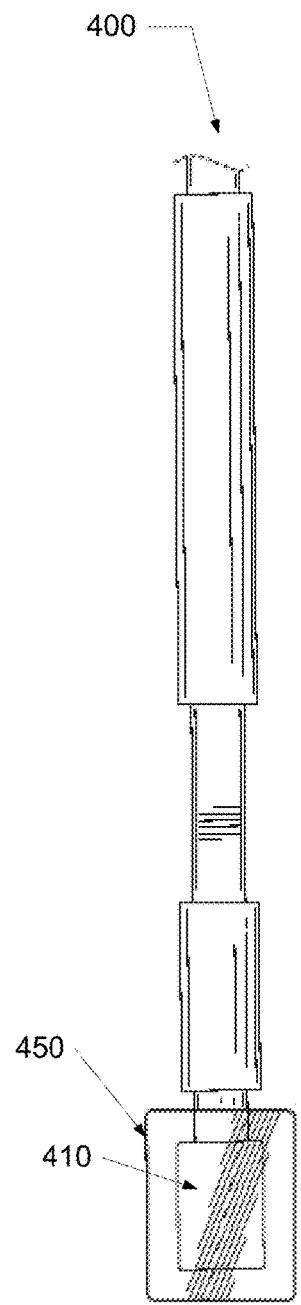
FIG. 4C shows a back view of the sensor probe shown in FIG. 4A.
Figure 4D:
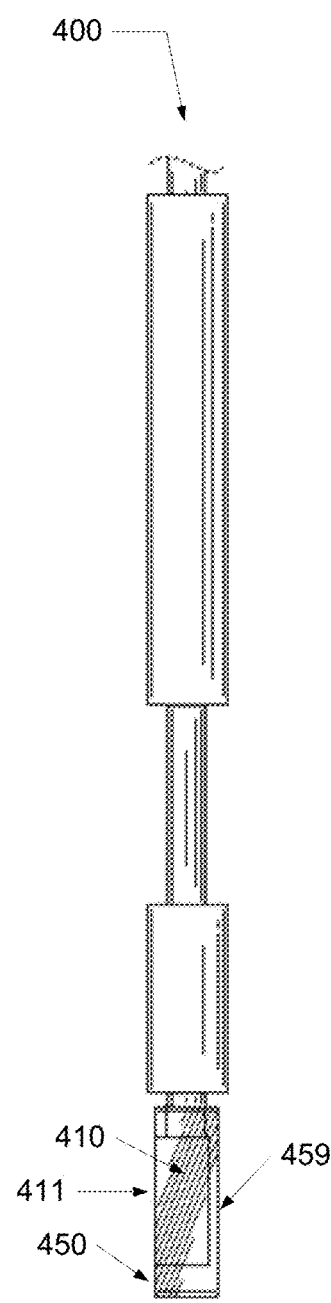
FIG. 4D shows a side view of the sensor probe shown in FIG. 4A.

FIG. 4C shows a back view of the sensor probe shown in FIG. 4A. FIG. 4D shows a side view of the sensor probe. The back surface of the sensor unit rests upon or is attached to a back wall 459 of the sheath member. Also, as shown in FIG. 4D, the scanning surface of the sensor unit is flushed with the lip region of the sheath member in this implementation.

Figure 4E:
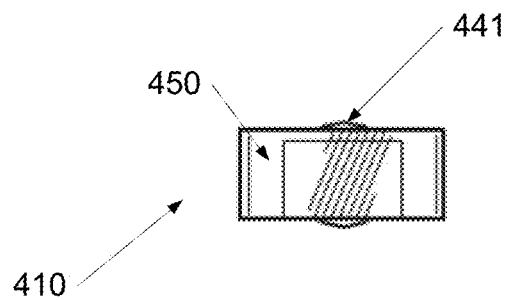
FIG. 4E shows a top view of the sensor probe shown in FIG. 4A.

FIG. 4E shows a top view of the sensor probe shown in FIG. 4A. FIG. 4E shows that the sensor unit is surrounded or embedded in the sheath member, except the scanning surface of the sensor unit. Behind the sensor unit assembly, a portion of the first tubing sleeve can be seen.

Figure 4F:
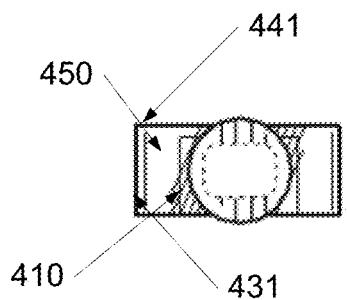
FIG. 4F shows a bottom view of the sensor probe shown in FIG. 4A, which is a view from the cable side.

FIG. 4F shows a bottom view of the sensor probe shown in FIG. 4A when the sensor probe is viewed from the cable side. The bottom view shows a cross section of first tubing sleeve 441. A dotted line 431 represents a cross section of the cable which is surrounded by the first tubing sleeve. Behind the first tubing sleeve is sheath member 450 and sensor unit 410 embedded in the sheath member.

Figure 4G:
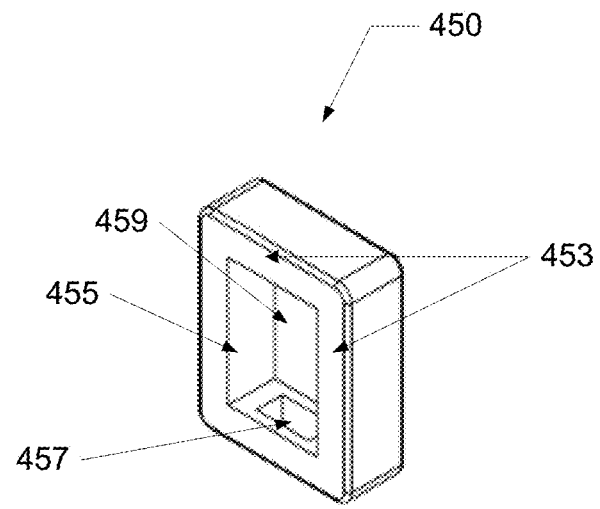
FIG. 4G shows a sheath member without a sensor unit embedded in it.

FIG. 4G shows sheath member 450 by itself without a sensor unit inserted in it. The sheath member has a recessed region 455 which is shaped to fit a sensor unit. The sheath member has a back wall 459 on which the sensor unit rests or is adhesively attached. A slot 457 on a bottom wall of the sheath member interconnects with the recessed region of the sheath member. The slot allows cable 431 which is connected to the sensor unit to exit from the sheath member. The sheath member also has a lip region 453 which surrounds the recessed region of the sheath member. The lip region refers to regions or walls around the recessed region where a surgical needle can thread from a top surface to a bottom surface of the sheath member to secure a sensor probe to a tissue.

The sheath member can be made of any suitable material. For example, the sheath member can be made of a solid elastomeric material which provides cushioning against a tissue. The terms "elastic" or "elastomeric" refer to any material which is capable of being elongated or deformed under an externally applied force, and which will substantially resume its original dimension or shape after the external force is released.

It is desired that an elastomeric material used to make a sheath member has sufficient softness so that it can be pierced and attached to a tissue by a surgical needle. For example, it is desired that a sheath member is made of an elastomeric material or a soft polymer that has a durometer shore A hardness (measured by ASTM D 2240) of between about 30 to about 70. In a specific implementation, a sheath member has a durometer shore A hardness of about 40.

It is desired that the material for a sheath member is sufficiently elastic so that it can be stretched to fit a sensor unit inside, and yet can withstand the weight of the sensor unit without tearing. In one implementation of the invention, elasticity of the sheath member is sufficient so that its slot can be stretched to fit a sensor unit through. For example, the sheath member (and also its slot) is capable of being elongated in at least one direction to an elongation of at least 50, 100, 200, 300, 400, 500, 600, or 700 percent of the original measurement of the sheath member. After inserting the sensor unit through the slot into the recessed region, the sheath member shrinks back down and surrounds and embeds the sensor unit in the recessed region, as well as the cable in the slot.

It is also desired that the material selected for a sheath member is a medical grade polymer which safe and inert in a body fluid, such as saliva. It is also desired that the material is transparent or translucent so that a tissue underneath the sheath member can be visualized when suturing a lip region of the sheath member onto a tissue.

Examples for a sheath member material include silastic or other silicone-based material, polyurethane, polyvinyl chloride silastic elastomers, silicone rubber, and others. In a specific implementation, the sheath member is made of a silicone material having a durometer shore A hardness of 40.

A sheath member can have any suitable shape as long as it can accommodate the size of a sensor unit and provides a lip region sufficiently wide enough to allow a surgeon to suture and secure the sensor unit onto a tissue. For a sensor unit that is in the shape of a rectangular block as shown in FIG. 4A, the recessed region of the sheath member is also similarly shaped (e.g., a rectangular block) to embed the sensor unit. However, the sheath member itself can be in any suitable shape, such as circular or elliptical cylinder as long as it provides sufficiently wide lip region for suturing.

In one implementation, a sensor unit assembly is suitably sized so that it can be used as an intraoral sensor probe in the oral cavity. It is desired that the sensor unit assembly fits into the oral cavity without causing much discomfort to a patient. Generally, a sensor unit assembly has a length and width less than 50 millimeters, more typically less than 30 millimeters. Also, a sensor unit assembly typically has a depth that is less than 20 millimeters, more typically less than 10 millimeters.

In a specific implementation, the sensor unit is in the shape of a rectangular block with a scanning surface of 12.4 millimeters (i.e., length) by 8.6 millimeters (i.e., width), and a depth of about 4.5 millimeters. The recessed region of the sheath member has approximately the same dimensions as the sensor unit so that the sensor unit can fit snugly into the recessed region of the sheath member.

The lip region of the sheath member surrounding the sensor unit is sufficiently wide so that a surgeon can pierce a surgical needle through the lip region to secure the sensor unit assembly to a tissue. Generally, the lip region is less than 10 millimeters wide, particularly when the sensor probe is used as an intraoral sensor probe. More typically, the lip region has a width is that is less than 5 millimeters. In a specific implementation, the lip region of the sheath member has a width of about 3 millimeters.

The sheath member can also have any suitable thickness as long as it securely holds the sensor unit in place. The sheath member can be thicker or thinner than the sensor unit, or have about the same thickness as the sensor unit. In other words, the scanning surface of the sensor unit can be flushed with a front surface of the sheath member. Alternatively, the scanning surface of the sensor unit can protrude slightly from the front surface of the sheath member. In a specific implementation, the sheath member has a thickness of about 5.5 millimeters, and its front surface is flushed with the scanning surface of the sensor unit as shown in FIGS. 4A and 4D. Also, as shown in FIG. 4A, the corners of the sheath members can be rounded to reduce point pressure applied to a tissue which contacts the sensor unit assembly.

As shown in FIG. 4G, the bottom wall of the sheath member has a slot 457, a rectangular opening, used to thread through a cable which is attached to the sensor unit. The slot is suitably sized so that it can be stretched sufficiently to fit a sensor unit through. Generally, the dimension of the slot is approximately the same or similar to the dimension of a portion of a cable proximate to the sensor unit. In a specific implementation, the slot has a dimension of about 5.1 millimeters by 2.5 millimeters.

The sheath member typically has a back wall 459 on which a back or rear surface of a sensor unit rests. The back wall of the sheath member can have any suitable thickness, typically less than 10 millimeters, more typically less than 3 millimeters. In a specific implementation, the back wall of the sheath member has a thickness of about 1 millimeter.

A sensor unit can be secured in a recessed region of a sheath member in a number of different ways. For example, the sensor unit can be secured in the recessed region of the sheath member by tension. Alternatively, it can be adhesively attached to the back surface of the sheath member. Any suitable adhesive can be used in bonding the sensor unit to the sheath member. It is desired that the adhesive is biocompatible. For instance, a silicon adhesive (e.g., Wacker Elastosil E951 silicone adhesive) can be used to bond the back surface of the sensor unit to the back wall of the sheath member.

As described and shown in FIG. 3, cable 431 operatively connects the sensor unit to a system unit or monitoring console, either electrically or optically, or both. In the implementation shown in FIG. 4A through 4D, a portion of the cable proximate to the sensor unit or the entire cable has a flattened cross section (e.g., see a rounded rectangular cross section 431 shown in FIG. 4F). The width of the cable shown in FIGS. 4B and 4C (viewed from front and back, respectively) is larger than the thickness of the cable shown in FIG. 4D (viewed from side).

A flattened cable portion proximate to the sensor unit provides several advantages. For example, since slot 457 in the sheath member is rectangular in shape, a cable with a rounded rectangular cross section has a better fit for the slot than a cable with a circular cross section. Thus, the shape of the cable will not distort the slot of the sheath member. Furthermore, a cable with a round or circular cross section may roll back and forth when sitting on a tissue. The rolling motion may interfere with optical measurements. A flattened cable portion provides a planar, stable region that would lay flat against the tissue, especially when the sensor unit assembly is sutured onto a flap tissue nearby.

In a specific implementation, a portion of the cable proximate to the sensor unit may have a width of about 6 millimeters (when viewed from front or back as shown in FIGS. 4B and 4C, respectively) and thickness of about 3 millimeters (when viewed from side as shown in FIG. 4D).

A flattened cable can be produced using any suitable methods. For example, the cable can be manufactured in a rectangular cable jacket. In another example, a portion of the cable nearby the sensor unit can be heat shrunken to have a rounded rectangular cross section. A cable with a flattened portion nearby the sensor unit allows a continuous transition from the cable to fit tightly into a rectangular slot of the sheath member.

Alternatively, a transitional junction tubing can be used to transition from a rectangular slot to a round cable. For example, a separate piece of heat shrink tubing can surround a circular cable adjacent to the sensor unit. The separate piece of tubing can be heat shrunken into a shape of flattened tubing at the junction point so that it better fills the rectangular slot of the sheath member. It can also prevent a rolling motion of a round cable.

In one implementation, a sensor probe may have one or more tubing sleeves surrounding a cable near a sensor unit assembly. For example, as shown in FIGS. 4A through 4D, some embodiments of the invention may include one or more tubing sleeves surrounding a sensor probe cable. A first tubing sleeve 441 is located adjacent to, but separated from, the sheath member. A second tubing sleeve 443 is separated from the first tubing sleeve and is located adjacent to the first tubing sleeve. Typically, the location of tubing sleeves can be adjusted by sliding them along the length of the cable. While inclusion of these tubing sleeves in a sensor probe is not necessary, they may provide several advantages when the sensor probe is used as an intraoral sensor probe.

A first tubing sleeve can be sutured to a tissue and serve as a secondary suture point to assist in stabilizing the sensor unit on a tissue. The first tubing sleeve can assist in decoupling a torsional force of a cable from the sensor unit. If the cable gets twisted around its length, then it can cause twisting of the sensor unit, lifting one or more sides of the sensor unit. Further, a torsional force of the cable can result in strain on suture points in the lip region of the sheath member surrounding the sensor unit. By providing additional suture points, a first tubing sleeve can provide a strain relief from torsional force, allowing the sensor unit to remain flat on the tissue.

A first tubing sleeve can have any suitable length as long as it is long enough to provide suture points to stabilize the sensor unit on a tissue. For example, it can have a length of at least 5 millimeters. When a sensor probe is used as an intraoral sensor, the first tubing is typically less than about 50 millimeters long so that it can be sutured at a secondary site within the oral cavity. In a specific implementation, the first tubing sleeve has a length of about 19 millimeters. Also, the first tubing sleeve has a suitable thickness so that it can be sutured. Typically, the first tubing sleeve wall has a thickness between about 1 millimeter to about 3 millimeters.

A first tubing sleeve is generally separated from the sensor unit assembly by some distance. For example, the first tubing sleeve is separated from a sensor unit assembly by at least about 1.5 millimeters. When a sensor probe including a first tubing sleeve is used as an intraoral sensor, the first tubing sleeve is typically separated from the sensor unit assembly by a distance up to about 25 millimeters. The separation or gap between the sensor unit assembly and the first tubing sleeve can provide strain relief by isolating movement of one sutured area from another area.

A first tubing sleeve can be made of any suitable material that is biocompatible. For example, the first tubing sleeve can be made of the same material as the sheath member. These include silastic or other silicone-based material, polyurethane, polyvinyl chloride silastic elastomers, silicone rubber, or others. In a specific implementation, a medical grade silicone tubing (e.g., RX-50 from Dow Corning) is selected as a first tubing sleeve.

It is also desired that the first tubing sleeve is transparent or translucent so a cable inside the first tubing sleeve is visible. The visibility of the cable inside the tubing sleeve assists a surgeon to avoid piercing the cable with a surgical needle when the tubing sleeve is sutured to a tissue.

In an implementation, a sensor probe also includes a second tubing sleeve 443 which covers and surrounds a portion of the cable nearby first tubing sleeve 441. The second tubing sleeve is typically separated away from the first tubing sleeve.

While a cable jacket protects optical fibers or electrical wires inside the cable, inclusion of a second tubing sleeve can provide an additional protection against biting or chewing by a patient inside the patient's oral cavity. Thus, the second tubing sleeve can protect against degradation of signal transmission in the cable. The second tubing sleeve can slide along the length of the cable, and its position can be adjusted between the upper and lower sets of teeth to protect the cable and signal transmission inside the cable.

The second tubing sleeve can be made of any suitable material that is biocompatible. In one implementation, the same material used to make a first tubing sleeve (see above) can be used to make a second tubing sleeve. Alternatively, different materials may be selected for the first tubing sleeve and second tubing sleeve.

While the implementation shown in FIGS. 4A through 4F shows an embodiment with the first and second tubing sleeves covering and protecting the cable, a sensor probe in another implementation may not include any tubing sleeves, or may include only a first tubing sleeve or a second tubing sleeve.

Embodiments of the invention can be applied to any suitable tissues to make optical measurements, such as oxygen saturation. A tissue may include any body parts, either animal or human. For example, a tissue may be skin, mucous membrane, graft, flap, and others.

In one implementation, a sensor probe in accordance with the present invention is applied to any tissue inside the oral cavity. For example, the sensor probe can be secured to any soft tissues including gum, tongue, cheek, or other areas where oxygen saturation measurements are desired.

In another specific implementation, a sensor probe in accordance with the present invention is applied on a flap tissue. A flap is a section of living tissue that carries its own blood supply and is moved from one area of the body to another. Flap surgery can restore form and function to areas of the body that have lost skin, fat, muscle movement, or skeletal support, or any combination of these.

Flap tissues may be comprised of one type of tissue or several different types of tissues. Examples of flaps composed of one type of tissue are skin (cutaneous), fascia, muscle, bone, and visceral (e.g., colon, small intestine) flaps. Examples of flaps that include several different types of tissues are fasciocutaneous (e.g., radial forearm flap), myocutaneous (e.g., transverse rectus abdominis muscle (TRAM) flap), osseocutaneous (e.g., fibula flap), tendocutaneous (e.g., dorsalis pedis flap), and sensory/innervated flaps (e.g., dorsalis pedis flap with deep peroneal nerve).

Flap tissues may be obtained from different locations of a body. For example, a local flap uses a piece of skin and underlying tissue that is located adjacent to the wound. The flap remains attached at one end so that it continues to be nourished by its original blood supply, and is repositioned over the wounded area. A regional flap uses a section of tissue that is attached by a specific blood vessel. When the flap is lifted, it needs only a very narrow attachment to receive its nourishing blood supply from the tethered artery and vein. A free flap is a section of tissue and skin that is completely detached from its original site and reattached to its recipient site by connecting all the micro vessels. When there is an adequate blood supply provided to a transplanted flap, the survivability of the transplanted flap is generally increased.

Using a sensor probe in accordance with the present invention, a flap can be monitored at various stages of surgery. For example, a sensor probe can be sutured to a flap tissue at its original site before any surgical procedures, and the blood supply and oxygen saturation of the tissue can be monitored before surgery, after lifting or elevating the tissue from its original site, during attachment to its recipient site, and during recovery. Since the oxygenation state of the tissue can be monitored at various stages, a sensor probe in accordance with the present invention provides a surgeon with an opportunity to take a remedial measure in the event that the condition of the tissue deteriorates. The surgeon need not wait after surgery and recover period to determine if a flap is successfully transferred.

In embodiments of the invention, any suitable surgical suturing technique can be applied to secure a sensor unit on a tissue. The choice of suture technique depends on the type and anatomic location of the wound, the thickness of the skin, the degree of tension, and others. Examples of suture techniques include an interrupted suture, a mattress suture, a running suture, and others.

In another aspect of the invention, a sensor probe in accordance with the present invention can be used without suturing a sheath member surrounding a sensor unit to a tissue. For example, a negative vacuum pressure can be applied to secure a sensor unit on a tissue to make oxygen saturation or other optical measurements. Particularly when a tissue is too delicate or fragile to suture a sensor unit assembly, a negative vacuum can be applied to secure the sensor unit or the sensor unit assembly on the tissue.

For example, a target tissue can be a wound bed itself. A wound can be pressure ulcers, diabetic ulcers, trauma wounds, burns, and others. The sensor probe can be placed directly on the wound bed to assess and monitor the wound where no flap or graft tissue is present at all.

In another example, a target tissue can be any type of flap tissue described above. A flap tissue which is incorporated into a recipient site can be monitored using the sensor probe, and the sensor unit of the sensor probe can be secured on the flap tissue by applying a negative vacuum pressure.

In yet another example, any graft tissue, particularly a fenestrated skin graft, can be monitored with a sensor probe in accordance with the present invention by applying a negative vacuum pressure. A fenestrated skin graft is a skin graft which is fenestrated with numerous puncture wounds or slits by means of a blade in order to aid the escape of any underlying fluid. A fenestrated skin graft can be secured to a recipient site in a patient and is covered during the healing process for a number of days (e.g., three to seven days) so that new vessels can be formed from the recipient bed.

Figure 5A:
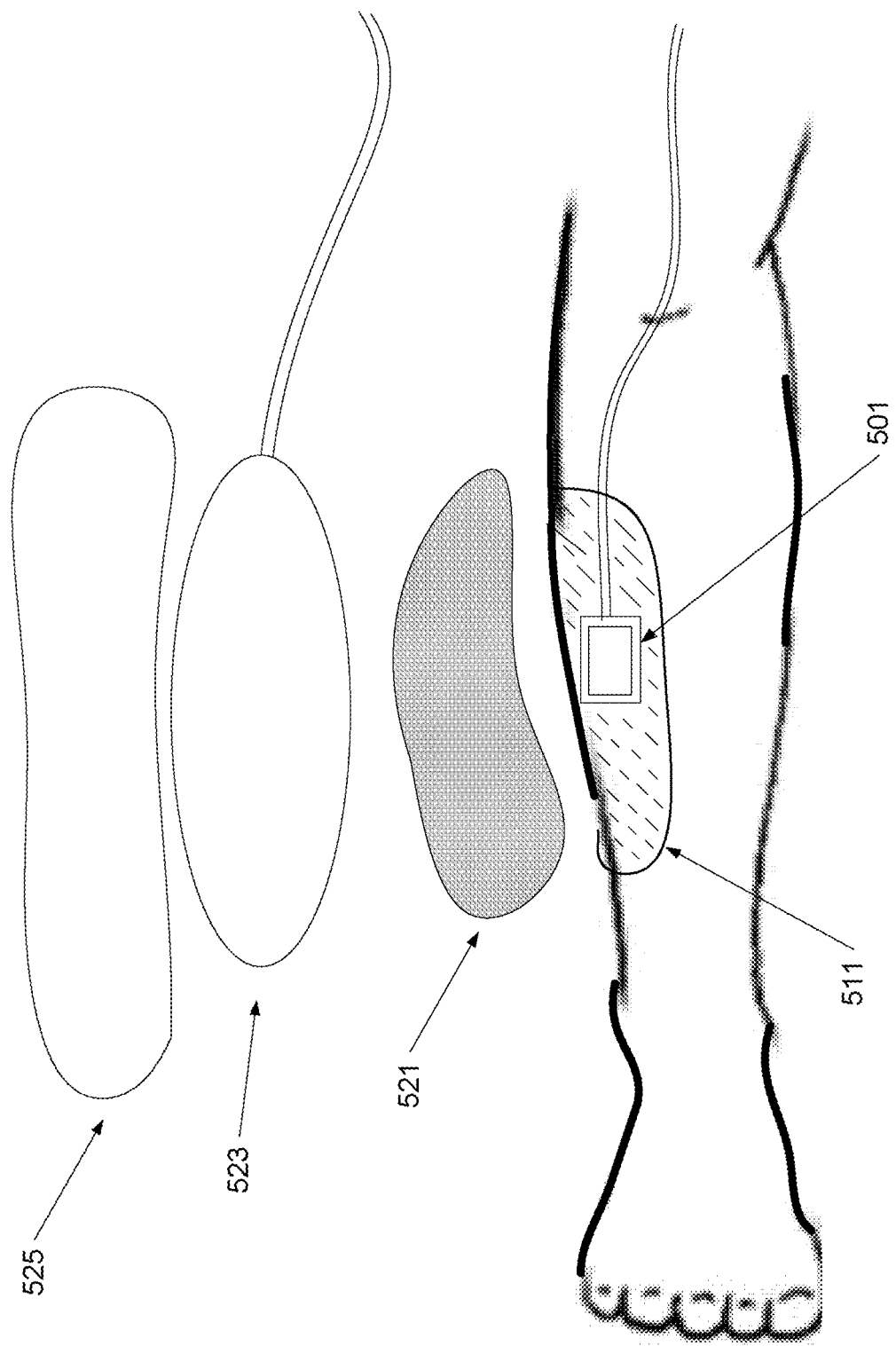
FIG. 5A shows a sensor unit assembly contacting a fenestrated skin graft over a patient's leg where the sensor unit assembly is secured by applying a negative vacuum pressure.

As shown in FIG. 5A, a sensor probe 501 in accordance with the present invention can be used to monitor the progress of skin graft healing and the formation of new vessels at the recipient site. FIG. 5 illustrates vacuum-assisted closure of skin graft in an ulcerated portion of a patient's leg using a vacuum device. A fenestrated skin graft 511 is placed over a lesion at a recipient site. A sensor unit assembly 501 is placed on top of the fenestrated skin graft with its scanning surface contacting the fenestrated skin graft. Above the sensor unit and fenestrated skin graft, a medical grade sponge dressing 521 (e.g., polyvinyl foam or polyurethane foam) is placed, typically over the entire wound surface to assist in removing wound exudates.

A vacuum plate 523 with a suction tube is subsequently placed over the sponge dressing. The suction tube of the vacuum plate is connected to a vacuum pump which is located on or nearby the patient. Negative pressure applied by the vacuum pump removes wound exudates into the sponge dressing as well as reduce extravascular, interstitial fluid from the tissue and improve blood supply to the graft area. Typically, negative pressure in the range of 5 to 15 kilopascals is applied continuously or intermittently. An adhesive drape 525 is applied over the vacuum plate to further secure all of the components together during the recovery period.

Figure 5B:
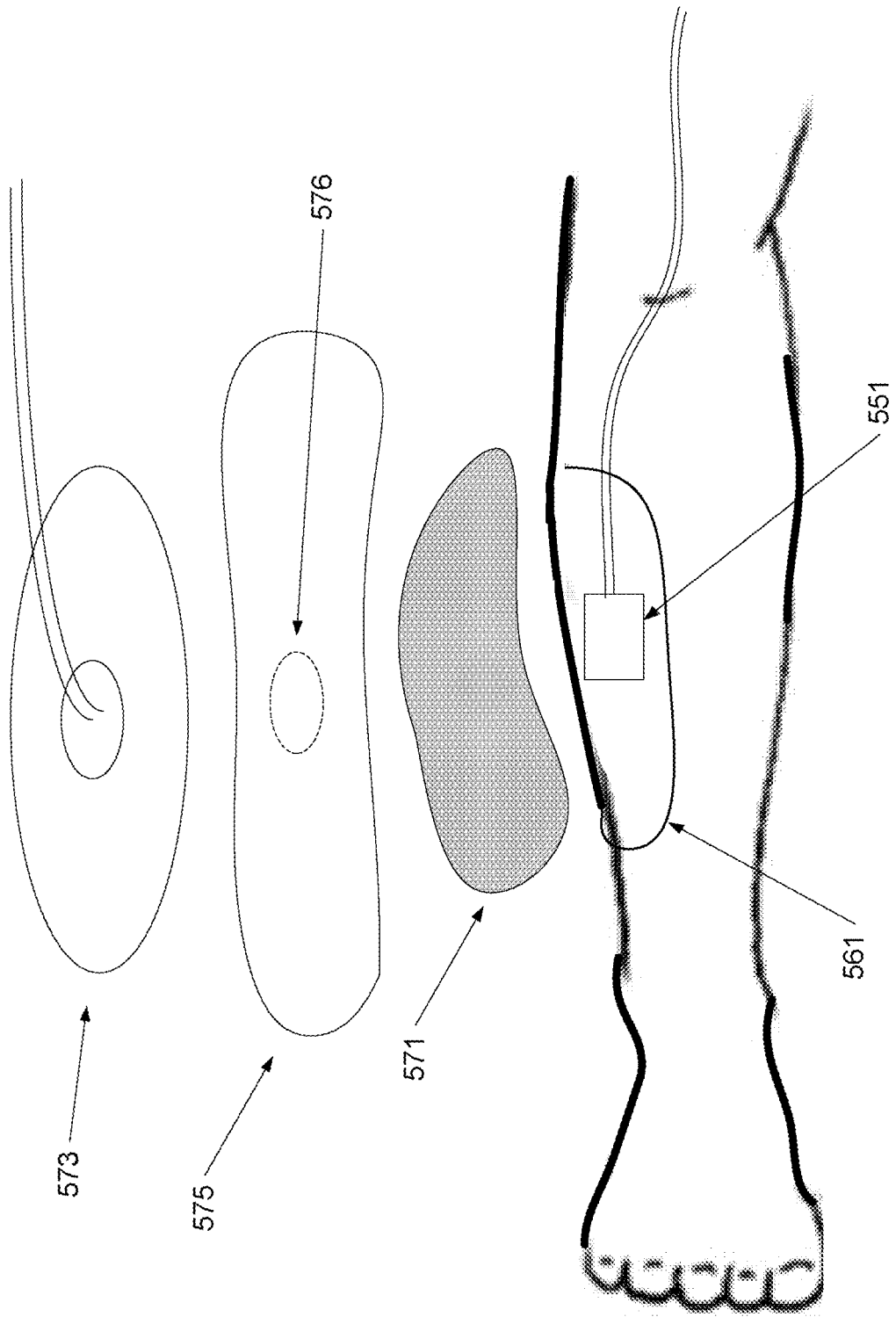
FIG. 5B shows a sensor unit contacting a wound bed in a patient's leg where the sensor unit is secured by applying a negative vacuum pressure.

FIG. 5B illustrates another implementation of vacuum-assisted closure of a wound bed and monitoring the healing process of the wound with a sensor unit. A sensor unit 551 (without a sheath member) is placed over a wound bed with its scanning surface contacting the wound bed. A sponge dressing 571 (which is about the size of the wound bed) is placed over the wound bed. An adhesive drape 575 which is larger than the size of the sponge dressing is placed over and covers the sponge dressing. Once the adhesive drape is in contact with the sponge dressing and skin surrounding the sponge dressing, a portion of the adhesive drape is pinched and a round hole (or other suitably shaped hole) 576 can be cut in the portion of the adhesive drape which covers the sponge dressing. Subsequently, a vacuum plate 573 is placed over the hole, and negative vacuum pressure can be applied.

As shown in FIGS. 5A and 5B, a sensor unit or sensor unit assembly is immobilized on a tissue by negative pressure and can monitor the healing process of the wound (or graft or flap tissue). As new vessels are formed in the wound bed or graft tissue, or as a blood flow through a flap tissue is stabilized, oxygen saturation readings from the sensor unit will improve over time. If oxygen saturation level decreases or does not improve over time, this may indicate that the wound is not healing properly or that a graft or flap tissue is failing to integrate at the recipient site. Rather than waiting several days to uncover whether the wound has properly healed, oxygen saturation or other optical measurements from the sensor unit can provide information regarding the healing process.

Following examples describe simulation and experimental results obtained by the optical systems and methods thereof according to the present invention. All simulation and experimental results indicate that the optical systems and methods thereof provide accurate predictions or measurements, or both, of the concentrations of the hemoglobins or the oxygen saturation, or both.

Example I

Suturing experiments were conducted on ex vivo animal tissue (e.g., a domestic fowl model) to determine which suturing method provides best stabilization of a sensor unit assembly. Shown in FIGS. 6A and 6B are sensor probes which are sutured onto an outer skin tissue using two different suturing methods.

Figure 6A:
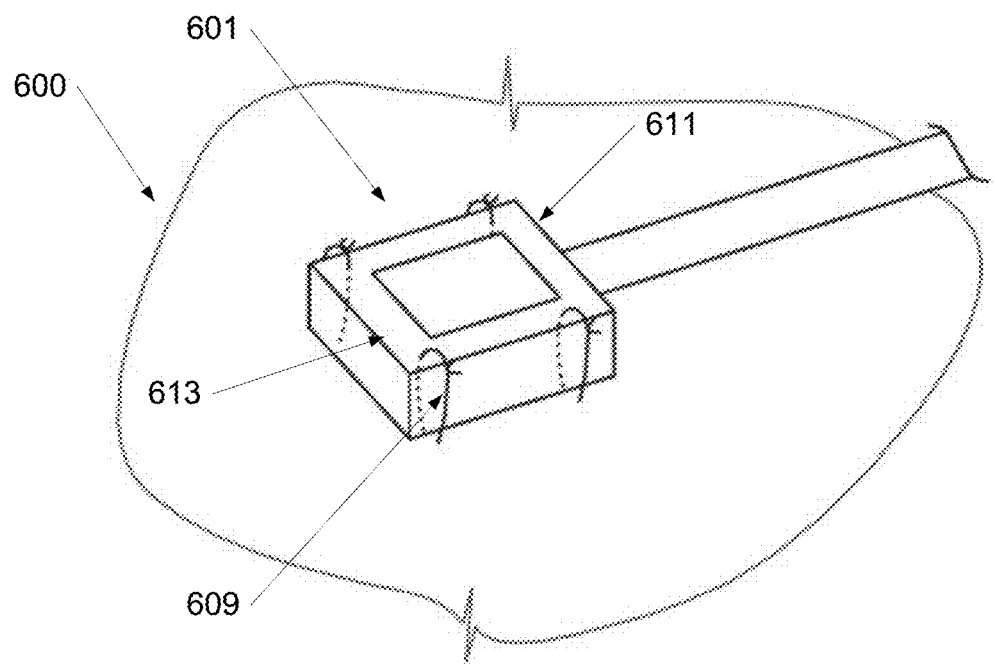
FIG. 6A shows a sensor unit assembly where its sheath member is sutured to a tissue by using an interrupted suture technique.

In FIG. 6A, a sheath member 611 of a sensor probe 601 was sutured to the animal tissue using interrupted sutures 609 at each corner of the sheath member. To form an interrupted suture, a surgical needle was passed through the thickness of a lip region 613 of the sheath member and pierced through the skin and then passed outside of the sheath member. Then the thread was pulled up to the original position and was knotted with the other end of the thread. The steps were repeated on three other corners of the sheath member.

Figure 6B:
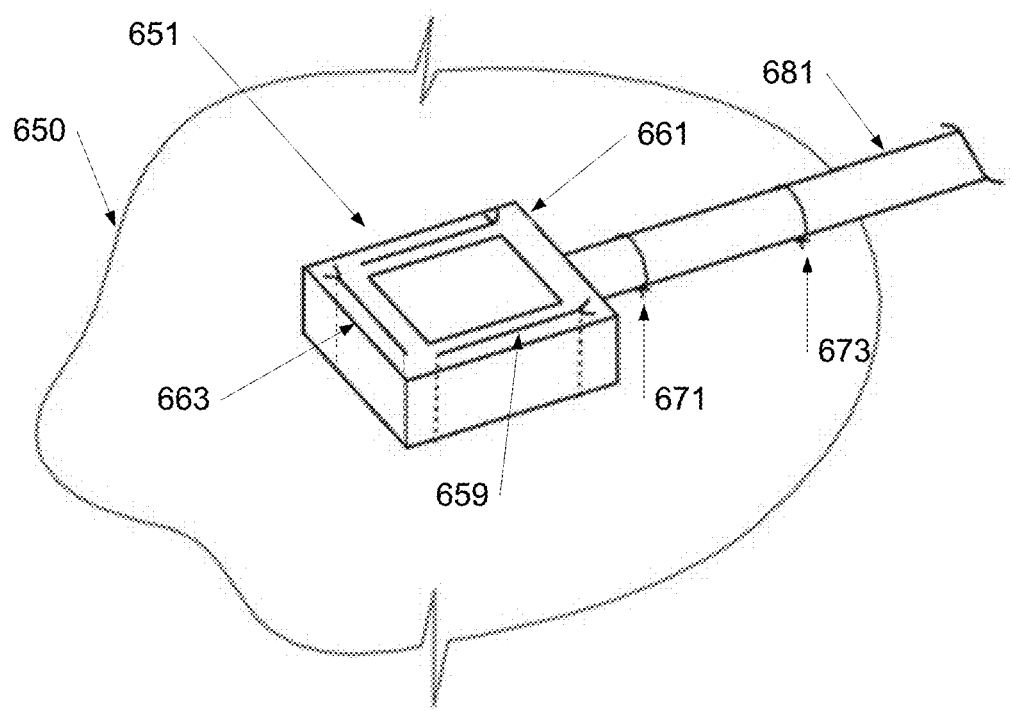
FIG. 6B shows a sensor unit assembly where its sheath member is sutured to a tissue by using a mattress suture technique.

In FIG. 6B, a sheath member 661 of a sensor probe 651 was sutured to an animal tissue 650 using mattress sutures 659 along three edges of the sheath member using 4-0 Ethilon with PS-4 cutting needle. A mattress suture was made by passing a suture through the thickness of a lip region 663 of the sheath member at one corner into the tissue and out through the skin and sheath member at an adjacent corner of the sheath member. Then the suture thread was pulled along the lip region of the sheath member to the point of origin, and a knot was tied. The steps were repeated along other edges of the sheath member.

The stabilities of the sensor units sutured on the animal tissue were compared. It was determined that the best fixation of the sensor unit assembly was obtained with mattress sutures, rather than with interrupted sutures. When a cable attached to the sensor unit was either pulled or lifted away from the sensor unit, the sensor unit assembly attached by mattress sutures was better fixated to the tissue and was less prone to movement.

As shown in FIG. 6B, two additional suture points 671 and 673 were added to a portion of a cable 681 proximate to the sensor unit. When a distal portion of the cable was pulled or lifted, the additional suture points on the cable effectively decoupled the cable movement from the sensor unit. In other words, the movement of the cable did not cause movement of the sensor unit assembly which was stitched on the animal tissue. Thus, the additional sutures over the cable provide strain relief and prevent sutures around the sensor unit from lifting when the cable is pulled or tugged by accident.

Example II

The effects of human bites on a cable containing optical fibers and signal quality factor were tested. If a sensor probe is used in oral flap monitoring, a patient could unintentionally bite the sensor cable. Tests were performed to determine the effects of tooth biting by a human on a sensor cable (or a cable with a short silicone tube sleeve around the cable).

As shown in FIG. 7A, the scanning surface of a sensor unit (not shown) was placed in contact with a phantom 711 using a band 713. The phantom mimics properties of a human tissue. A transparent silicon tubing sleeve 725 was placed over a portion of a cable 723 connected to the sensor unit.

Two different types of tubing sleeves were used. In a first test, the following silicon tubing sleeve was used—Silastic laboratory tubing catalog number 515-013 (Dow Corning, Midland, Mich.) with an inner diameter of 4.78 millimeters and an outer diameter of 7.92 millimeters (i.e., a wall thickness of 1.57 millimeters). In a second test, the following silicon tubing was used—Silastic laboratory tubing catalog number 515-014 (Dow Corning, Midland, Mich.) with an inner diameter of 4.78 millimeters and an outer diameter of 9.53 millimeters (i.e., a wall thickness of 2.38 millimeters).

For both tests, the part of the cable that had a silicon tubing sleeve was bitten by the first molar teeth (the third pair from the back) on the right. The bite was light during the first 5 seconds or so, then moderate in the following 5 seconds or so, then hard for another 5 seconds or so, and finally extremely hard for another 5 seconds or so.

FIG. 7B shows the effects of bites of varying strength on signal quality factor for the first test with the silicon tubing sleeve having a wall thickness of 1.57 millimeters. The baseline signal quality factor for control (i.e., no bites) was about 95. A signal quality factor is a number which indicates, among other things, whether the sensor unit is in good contact with tissue, and whether the oximeter of which the sensor unit is a part is in good working order. When all the measurement conditions are optimal, the signal quality factor has a value of approximately 100. Techniques for calculating signal quality factor are described in U.S. patent application Ser. No. 11/162,380, filed Sep. 8, 2005, and U.S. patent application Ser. No. 12/126,860, filed May 24, 2008, which are incorporated by reference.

As shown in FIG. 7B, when the silicon tubing sleeve with a thinner wall was bitten with a light bite, followed by a moderate bite, the signal quality factor remained about the same as the control. However, when the silicon tubing sleeve was bitten by a hard bite or extreme hard bite, the signal quality factor degraded substantially as shown in FIG. 7B. This drop in signal quality factor indicated the damage of glass fiber bundles inside the cable, and signal quality factor could be used as an indicator for fiber damage.

This result indicates that a silicon tubing sleeve with a thinner wall provided signal quality protection against fiber damage when the cable was bitten either lightly or moderately. However, the wall thickness of the silicon tubing sleeve was not sufficient to protect signal quality when the silicon tubing sleeve was bitten by hard bites or extremely hard bites.

FIG. 7C shows the effects of bites of varying strength on signal quality factor for the second test with the silicone tubing sleeve having a wall thickness of 2.38 millimeters. The baseline signal quality factor for control (i.e., no bites) was about 97. As shown in FIG. 7C, the signal quality factor remained about the same as the control throughout the time period in spite of the fact that the silicon tubing sleeve was bitten with different force. This result indicates that the silicon tubing having a wall thickness of 2.38 millimeters can provide signal quality protection against all types of human bites.

An additional test was performed to determine how much protection a cable jacket itself provides against human bites. An empty cable jacket (without glass fiber bundles inside) which was used to make a cable was tested using the same bite protocol described above with respect to FIG. 7A. A white polyvinyl chloride jacket (SLV-105-13; Insultab #4900 from Ico-Rally) was used to as a cable jacket.

The test results indicate that the harder the bite, the more extensive dent was on the cable jacket. However, in spite of extreme bites and chewing, no tears or holes could be produced in the polyvinyl chloride jacket. Thus, this result indicates that a cable jacket itself may be sufficient to protect a patient from internal glass fiber bundles when the patient bites or chews the cable unintentionally.

FIGS. 8A through 8H show various configurations of source structures and detector structures in a sensor unit. Each figure shows a particular opening pattern. The openings in the figures can be either source structures or detector structures, and they may be referred to herein as an opening or openings in FIGS. 8A through 8H. While the figures show only some examples of opening patterns, other opening patterns may be used with embodiments of the invention.

Figure 8A:
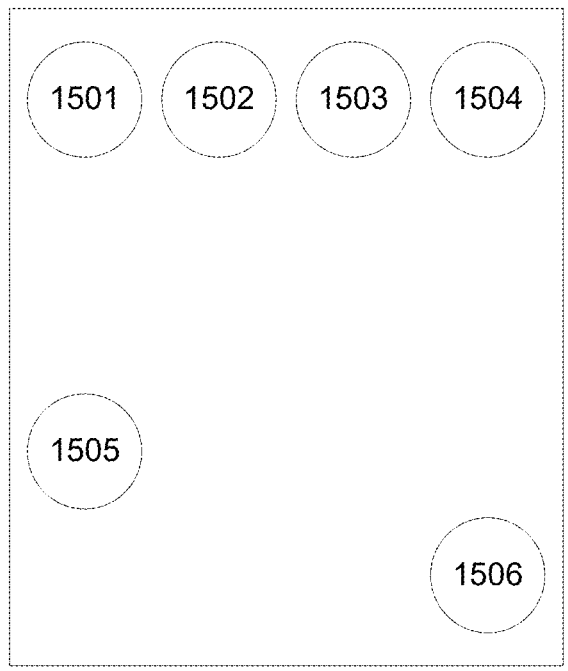
FIG. 8A shows a sensor opening pattern where one sensor opening is aligned asymmetrically with respect to the other sensor openings.

FIG. 8A shows a specific implementation of an oximeter sensor unit. This oximeter sensor unit has six openings 1501-1506. Openings 1501-1504 are arranged in a line closer to a first edge of the oximeter sensor unit, while openings 1505 and 1506 are arranged closer to a second edge, which is opposite the first edge. In fact, opening 1506 is closer than opening 1505 to the second edge. In an implementation, the first edge is distal to the second edge, which is closer to a cable attached to the sensor panel.

In this implementation, the oximeter sensor unit has a rectangular shape, but the oximeter sensor unit may have any shape such a trapezoid, triangle, dodecagon, octagon, hexagon, square, circle, or ellipse. An oximeter sensor unit of any shape or form can incorporate the sensor openings in the pattern shown and described.

In one implementation, openings 1501-1504 are detector structures while openings 1505 and 1506 are source structures. However, in other implementations, there can be one or more detector structures, two or more detector structures, one or more source structures, or two or more source structures. For example, there may be three detector structures and three source structures or one detector structures and five source structures.

In FIG. 8A, the openings are positioned asymmetrically such that a line drawn through openings 1501-1504 is not parallel to a line drawn through openings 1505 and 1506. However, a line drawn through openings 1501 and 1505 is parallel to a line through openings 1504 and 1506. Additionally, the distance between openings 1501 and 1504 is shorter than the distance between openings 1505 and 1506.

Thus, the distance between openings 1501 and 1505 does not equal the distance between openings 1501 and 1506; the distance between openings 1502 and 1505 does not equal the distance between openings 1503 and 1505; and the distance between openings 1503 and 1505 does not equal the distance between openings 1504 and 1506.

In a specific implementation, a line drawn through openings 1501 and 1505 is perpendicular to a line drawn through openings 1501 and 1504. Also, a line drawn through openings 1501 and 1504 is perpendicular to a line drawn through openings 1504 and 1506.

In a specific implementation, a distance between openings 1501 and 1504 is five millimeters. A distance between each of the openings 1501, 1502, 1503, and 1504 is 5/3 millimeters. A distance between 1501 and 1505 is five millimeters. A diameter of an opening is one millimeter.

Figure 8B:
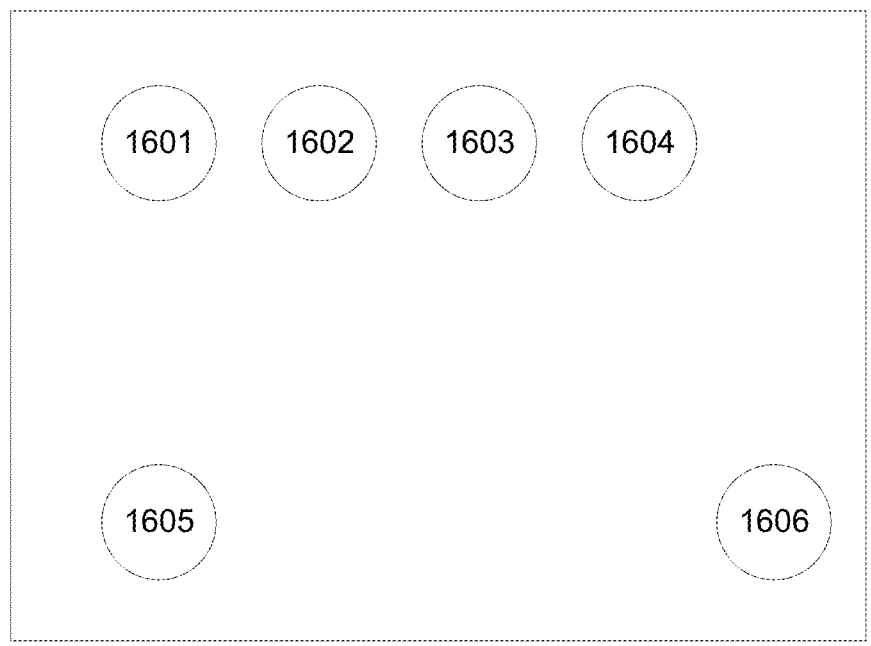
FIG. 8B shows another sensor opening pattern where one sensor opening is aligned asymmetrically with respect to the other sensor openings.

FIG. 8B shows a variation of the implementation of the oximeter sensor unit shown in FIG. 8A. The oximeter sensor unit in this specific implementation is also arranged to include six openings 1601-1606. Similar to FIG. 8A, openings 1601-1604 are arranged in a line closer to a first edge of the sensor, while openings 1605 and 1606 are arranged closer to a second edge, which is opposite the first edge. In one implementation, openings 1601-1604 are detector structures while openings 1605 and 1606 are source structures.

In this figure, the openings are positioned so that a line drawn through openings 1601-1604 is parallel to a line through openings 1605 and 1606. However, a line drawn through openings 1601 and 1605 is not parallel to a line through openings 1604 and 1606.

Additionally, similar to FIG. 8A, the distance between openings 1601 and 1604 is shorter than the distance between openings 1605 and 1606. Thus, the distance between openings 1601 and 1605 does not equal the distance between openings 1601 and 1606; the distance between openings 1602 and 1605 does not equal the distance between openings 1603 and 1605; and the distance between openings 1603 and 1605 does not equal the distance between openings 1604 and 1606.

In this implementation, the oximeter sensor unit itself is of a greater area relative to the area of the oximeter sensor unit shown in FIG. 8A. In another implementation, the oximeter sensor unit may be of a smaller area relative to the area shown in FIG. 8A. In yet another implementation, the oximeter sensor unit may be of a greater area relative to that shown in FIG. 2B.

Further, in a specific implementation, the openings are the same size as each other (e.g., each opening has the same diameter or each opening has the same area). A specific implementation uses one-millimeter circular openings. However, in another implementation, the diameter of one opening may be different from other openings, or there may be some openings with different diameters than other openings. There can be any combination of differently sized openings on one oximeter sensor unit. For example, there are two openings with a C size and other openings have a D size, where C and D are different and D is greater than C. Also, openings are not necessarily circular. So, C and D may represent area values.

Figure 8C:
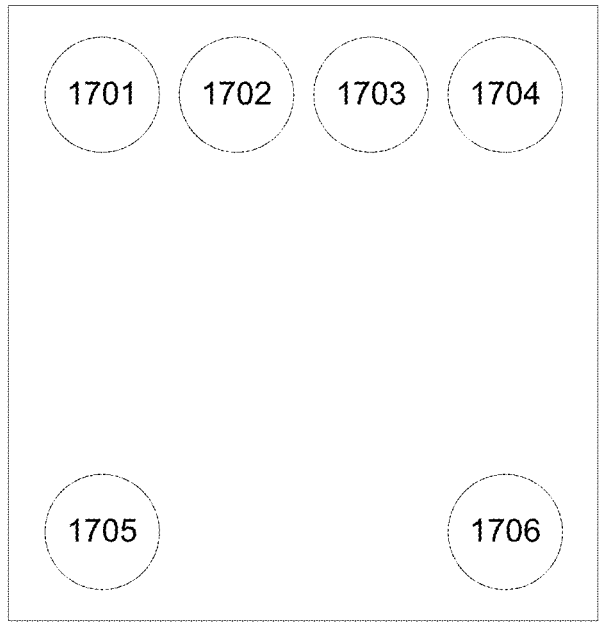
FIG. 8C shows a sensor opening pattern where the openings are arranged symmetrically about a vertical axis.

FIG. 8C shows another variation of the implementation of the oximeter sensor unit shown in FIG. 8A. The oximeter sensor unit in this specific implementation is also arranged to include six openings 1701-1706. Similar to FIGS. 8A and 8B, openings 1701-1704 are arranged in a line closer to a first edge of the sensor, while openings 1705 and 1706 are arranged closer to a second edge, which is opposite to the first edge. In one implementation, openings 1701-1704 are detector structures while openings 1705 and 1706 are source structures.

In this figure, the openings are positioned so that a line drawn through openings 1701-1704 is parallel to a line through openings 1705 and 1706. In fact, these two lines are equal in length. Furthermore, a line drawn through openings 1701 and 1705 is parallel (and equal in length) to a line through openings 1704 and 1706.

Thus, in this specific implementation, the distance between openings 1701 and 1706 is equal to the distance between openings 1704 and 1705. This specific arrangement includes further equalities: the distance between openings 1702 and 1705 equals that between openings 1703 and 1706 and the distance between openings 1703 and 1705 equals that between openings 1702 and 1706.

In an implementation, the distances between openings 1701-1704, 1704-1706, 1706-1705, and 1705-1701 are all equal; thus, in this implementation openings 1701, 1704, 1706, and 1705 form the vertices of a square. In other implementations, however, four openings may form the vertices of any quadrilateral, such as a rectangle, a rhombus, a trapezoid, or a parallelogram.

Aside from the equalities mentioned, the distances between each of the openings 1701-1704 and each of the openings 1705-1706 are not equal. For instance, the distance between openings 1701 and 1705 does not equal the distance between openings 1701 and 1706.

Figure 8D:
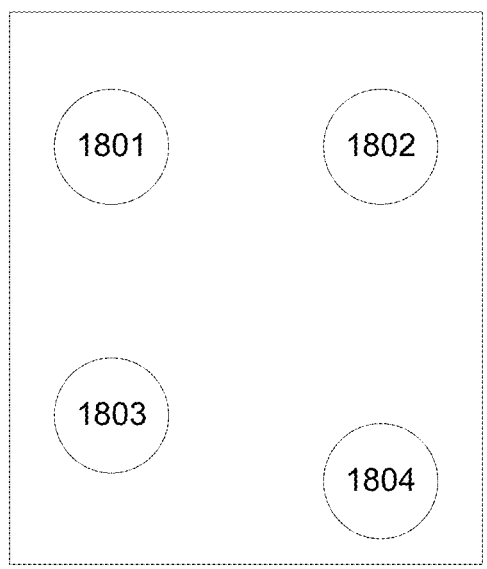
FIG. 8D shows another sensor opening pattern where one sensor opening is aligned asymmetrically with respect to the other sensor openings.

FIG. 8D shows a specific implementation of an oximeter sensor unit which is arranged to include four openings 1801-1804. Openings 1801 and 1802 are arranged in a line closer to a first edge of the sensor, while openings 1803 and 1804 are arranged closer to a second edge, which is opposite the first edge. In fact, opening 1804 is closer than opening 1803 to the second edge.

In one implementation, openings 1801 and 1802 are detector structures and openings 1803 and 1804 are source structures. However, in other implementations, there can be one or more detector structures, two or more detector structures, one or more source structures, or two or more source structures. For example, there may be three detector structures and one source structure or one detector structure and three source structures.

In FIG. 8D, the openings are positioned asymmetrically such that a line drawn through openings 1801 and 1802 is not parallel to a line through openings 1803 and 1804. However, a line drawn through openings 1801 and 1803 is parallel to a line through openings 1802 and 1804.

Additionally, the distance between openings 1801 and 1802 is shorter than the distance between openings 1803 and 1804. Thus, in FIG. 8D, the distance between openings 1801 and 1803 does not equal the distance between openings 1802 and 1804 and the distance between openings 1802 and 1803 does not equal that between openings 1802 and 1804.

Figure 8E:
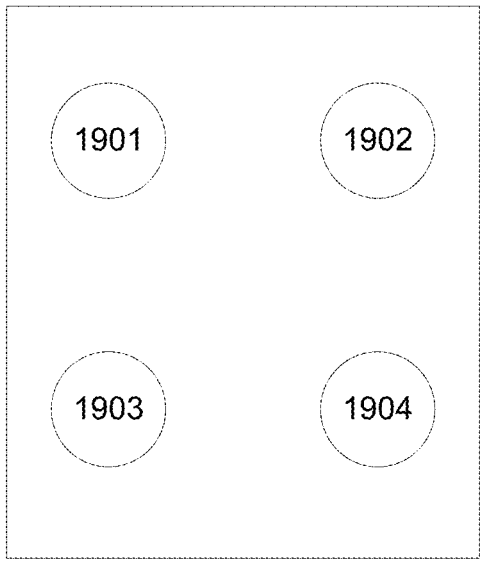
FIG. 8E shows a sensor opening pattern where the openings are arranged symmetrically about horizontal and vertical axes.

FIG. 8E shows a variation of the implementation of the oximeter sensor unit shown in FIG. 8D. The oximeter sensor unit of this implementation also includes four openings 1901-1904. Openings 1901 and 1902 are arranged in a line closer to a first edge of the oximeter sensor unit, while openings 1903 and 1904 are arranged closer to a second edge, which is opposite the first edge. In one implementation, openings 1901 and 1902 are detector structures and openings 1903 and 1904 are source structures.

In FIG. 8E, the openings are positioned symmetrically such that a line drawn through openings 1901 and 1902 is parallel, and equal, to a line through openings 1903 and 1904. Additionally, a line drawn through openings 1901 and 1903 is parallel, and equal, to a line through openings 1902 and 1904.

In an implementation, the distances between openings 1901-1902, 1902-1904, 1904-1903, and 1903-1901 are all equal; thus, in this implementation openings 1901, 1902, 1903, and 1904 form the vertices of a square. In other implementations, however, four openings may form the vertices of any quadrilateral, such as a rectangle, a rhombus, a trapezoid, or a parallelogram.

Some of the distances between the centers of particular openings are unequal; for instance, the distance between openings 1901 and 1903 does not equal the distance between openings 1901 and 1904.

Figure 8F:
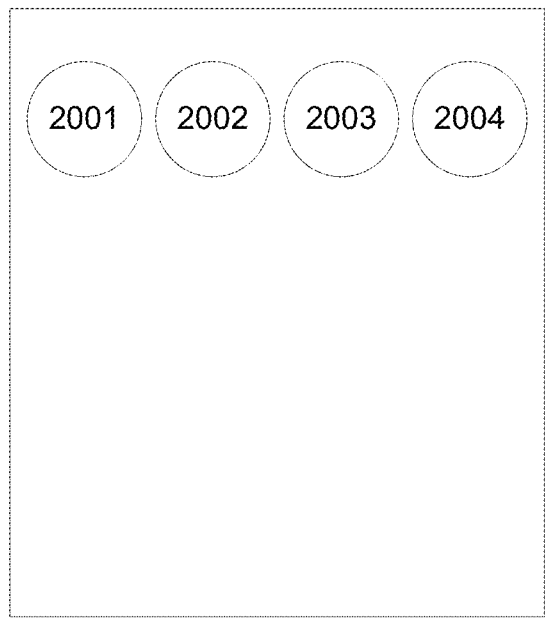
FIG. 8F shows a sensor opening pattern where the openings are aligned in a row.

FIG. 8F shows another variation of the implementation of the oximeter sensor unit shown in FIG. 8D. Similar to FIGS. 8D and 8E, this specific implementation of an oximeter sensor unit includes four openings 2001-2004.

However, in this variation, all four of the openings are arranged in a line closer to a first edge of the sensor. Specifically, in this figure, openings 2001-2004 lie in a row parallel to the first edge so that a straight line may be drawn through each opening. In one implementation, openings 2001 and 2002 are detector structures and openings 2003 and 2004 are source structures.

In this specific implementation, the distance between openings 2001 and 2002 is equal to the distance between openings 2002 and 2003; this distance is also equal to that between openings 2003 and 2004.

Additionally, the distance between openings 2001 and 2003 equals that between openings 2002 and 2004. In fact, this distance is twice the distance between each individual opening. Thus, the distance between openings 2001 and 2003 does not equal that between openings 2001 and 2002; the former is twice the distance of the latter.

Figure 8G:
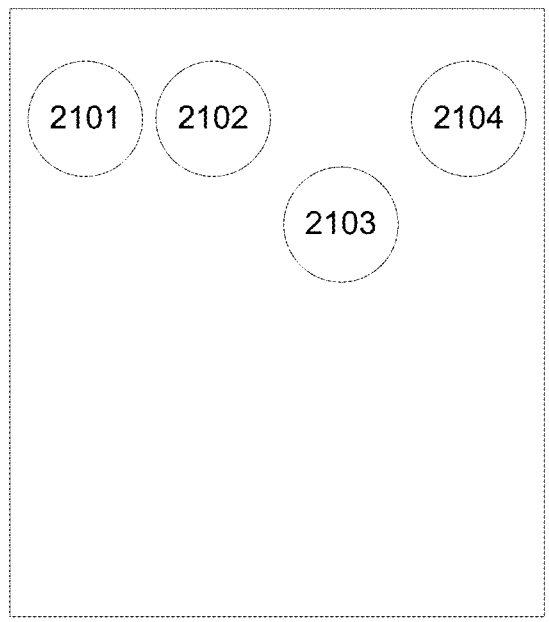
FIG. 8G shows a sensor opening pattern where the openings are aligned in a row, except for one of the openings.
Figure 8H:
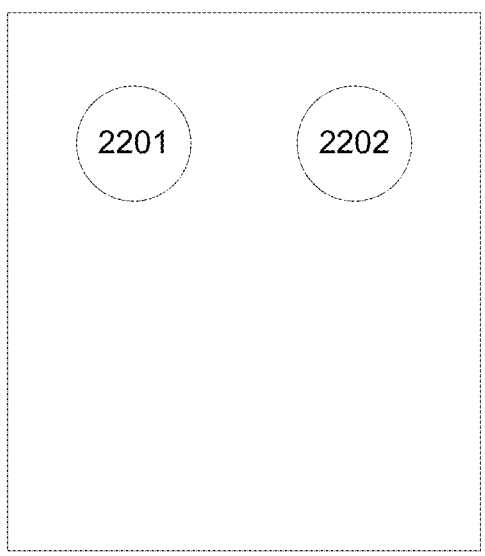
FIG. 8H shows a sensor opening pattern with two openings.

FIG. 8G shows a variation of the implementation of the oximeter sensor unit shown in FIG. 8H. This implementation of an oximeter sensor unit is similarly arranged to include four openings 2101-2104. Also, this arrangement of openings is located closer to a first edge of the sensor. However, in this figure, openings 2101, 2102, and 2104 lie in a row parallel to the first edge so that a straight line may be drawn through the center of each opening, while opening 2103 lies below that straight line.

In this implementation, opening 2103 lies equally spaced between openings 2102 and 2104; in other implementations, opening 2103 can lie closer to one opening than another. In one implementation, openings 2101 and 2102 are detector structures and openings 2103 and 2104 are source structures.

In this specific implementation, as mentioned above, the distance between openings 2102 and 2103 equals that between openings 2103 and 2104. Aside from this equality, the distances between the openings are unequal. For example, in this implementation, the distance between openings 2101 and 2103 does not equal the distance between openings 2102 and 2104, and the distance between openings 2102 and 2103 does not equal that between openings 2102 and 2104.

FIG. 8H shows a specific implementation of an oximeter sensor unit which is arranged to include two openings 2201 and 2202. Similar to FIGS. 8F and 8G, this arrangement of openings is located closer to a first edge of the oximeter sensor unit. Additionally, openings 2201 and 2202 lie in a row parallel to the first edge so that a straight line may be drawn through each opening. In one implementation, opening 2201 is a detector structure and opening 2202 is a source structure.

Although oximeter sensor units with two, four, and six openings are shown in these figures, other implementations may include different numbers of oximeter sensor unit openings. For instance, there may be three, five, seven, eight, or more openings.

Further, there may be any combination of detector structures and source structures and the number of detector structures need not equal the number of source structures. For instance, if there are three openings, there may be one detector structure and two source structures or two detector structures and one source structure. As another example, if there are eight openings, there may be two detector structures and six source structures, five detector structures and three source structures, or four detector structures and four source structures.

The distance between one opening to another (e.g., between a source structure and a detector structure) in an oximeter sensor unit can also vary depending on many factors including the nature and the depth of a tissue to be examined. In one embodiment, a source structure and a detector structure may be separated by about 20 millimeters. In another embodiment, a source structure and a detector structure may be separated by about 10 millimeters. In another embodiment, a source structure and a detector structure may be separated by about 5 millimeters. In yet another embodiment, a source structure and a detector structure may be separated by 2 millimeters. Many other variations of opening distances can be implemented in embodiments of the present invention.

There are various other implementations of sensor opening patterns which can be incorporated into a sensor unit. Some of these implementations are discussed in U.S. patent application Ser. No. 12/126,860, filed May 24, 2008, U.S. patent application Ser. No. 12/178,359, filed Jul. 23, 2008, and U.S. Pat. No. 7,355,688. These patent and patent applications are assigned to the same assignee as this patent application and are incorporated by reference. Any of the asymmetrical or symmetrical arrangements of sources and detectors discussed in that patent is applicable to the source structures and detector structures in this application.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A sensor probe comprising:
a sensor unit comprising a first source structure and a first detector structure on a scanning surface of the sensor unit, wherein the first source structure comprises an opening that is coupled to a distal end of a first optical fiber, and the first detector structure comprises an opening that is coupled to a distal end of a second optical fiber;
an elastomeric sheath member comprising a silicone-based material and having a recessed region for embedding the sensor unit and a lip region surrounding the scanning surface of the sensor unit,
wherein the elastomeric sheath member comprises an elastomeric material having greater elasticity than the sensor unit and the elastomeric sheath member comprises a solid translucent material, without prefabricated suture openings extending through, adapted for suturing the elastomeric sheath member with the sensor unit onto tissue,
the recessed region comprises an opening and an inside surface, opposite to the opening,
the scanning surface of the sensor unit comprising the first source structure and first detector structure faces in a direction away from the inside surface, and
when the first source structure and first detector structure of the scanning surface are placed against a tissue to be evaluated, the first source structure emits a first light into the tissue without passing through the elastomeric sheath member, and the first detector structure receives a second light reflected from the tissue, and
the solid translucent material forms at least a portion of the lip region and the portion of the lip region comprising the solid translucent material is designed to be sutured from a first pierceable surface to a second pierceable surface, opposite of the first pierceable surface, of the lip region onto tissue without having sutures entering the recessed region where the sensor unit is embedded;
a cable connected to the sensor unit wherein the cable is configured to operably couple the sensor unit to a system unit, wherein the cable comprises the first optical fiber that couples the first source structure to a first light emitter diode and the second optical fiber that couples the first detector structure to a first photodetector;
a first tubing sleeve, covering a first portion of the cable, wherein the first tubing sleeve comprises a channel through which the cable passes through, and a first position is separated from the elastomeric sheath member by a first gap; and
a second tubing sleeve, covering a second portion of the cable, wherein the second tubing sleeve comprises a channel through which the cable passes through, a second position is separated from the first tubing sleeve by a second gap, larger than the first gap, and the first tubing sleeve is between the elastomeric sheath member and the second tubing sleeve.

2. The sensor probe of claim 1 wherein the second light reflected from the tissue is received by the first detector structure without passing through the elastomeric sheath member.

3. The sensor probe of claim 1 wherein the lip region of the sheath member can be pierced by a surgical needle.

4. The sensor probe of claim 1 wherein the sheath member is comprised of a silicone material.

5. The sensor probe of claim 1 wherein the sensor probe is an intraoral sensor probe, and the elastic sheath member is suturable to tissue of an oral cavity.

6. The sensor probe of claim 1 wherein the sheath member has a slot which is interconnected to the recessed region on a bottom wall of the sheath member, wherein the slot is configured to fit a portion of the cable proximate to the sensor unit.

7. The sensor probe of claim 1 wherein the elastomeric material is elongated in at least one direction to an elongation from at least about 50 to about 700 percent.

8. The sensor probe of claim 1 wherein a portion of the cable proximate to the sensor unit is flattened, and the flattened cable fits into a rectangular slot of the elastomeric sheath member.

9. The sensor probe of claim 1 further comprising the first tubing sleeve, covering a first portion of the cable nearby the sensor unit, wherein the first tubing sleeve is suturable, and comprises a transparent or translucent material.

10. The sensor probe of claim 9 further comprising the second tubing sleeve, covering a second portion of the cable, which is located nearby the first tubing sleeve, and the second tubing sleeve is slidably coupled to the cable to alter a distance from the first tubing sleeve, whereby the second tubing sleeve cushions the cable from the effect of mouth bite pressure on the cable.

11. The sensor probe of claim 10 wherein the first tubing sleeve, the second tubing sleeve, or both comprise a silicone material.

12. The sensor probe of claim 1 wherein the sensor unit further comprises a second source structure and a second detector structure,
wherein a first distance is between the first source structure and the first detector structure, a second distance is between the first source structure and the second detector structure, a third distance is between the second source structure and the first detector structure, a fourth distance is between the second source structure and the second detector structure, and the first distance is not equal to the fourth distance and the second distance is not equal to the third distance.

13. The sensor probe of claim 12 wherein the sensor unit further comprises a third detector structure and a fourth detector structure which are located between the first detector structure and the second detector structure, wherein all of the detector structures are linearly aligned with respect to one another, wherein
  a distance between the first detector structure and the second detector structure is 5 millimeters,
  a distance between adjacently located detector structures is 5/3 millimeters, and
  a distance between the first detector structure and the first source structure is 5 millimeters.

14. A method comprising:
  contacting the scanning surface of the sensor probe of claim 1 on a tissue;
  securing the sensor probe on the tissue by piercing and suturing the lip region of the elastomeric sheath member to the tissue with a suturing needle;
  transmitting the first light through the first source structure into the tissue;
  receiving the second light transmitted through the tissue at the detector structure; and
  determining an oxygen saturation value for the tissue based on values for the first and second light.

15. The method of claim 14 wherein the tissue is a flap tissue inside an oral cavity.

16. The method of claim 15 wherein the sensor probe further comprises the first tubing sleeve covering a first portion of the cable nearby the sensor unit, wherein the first tubing sleeve comprises a transparent or translucent material, and wherein the method further comprises suturing the first tubing sleeve to the flap tissue or a tissue adjacent to the flap tissue.

17. The sensor probe of claim 1 wherein a back surface of the sensor unit, opposite to the scanning surface, is positioned against the inside surface of the recess,
  whereby when the sensor probe is placed against a tissue to be evaluated, the inside surface of the recess urges, via the back surface, the scanning surface of the sensor unit against the tissue.

18. The sensor probe of claim 1 wherein the scanning surface of the sensor unit protrudes from the opening of the recessed region such that the scanning surface is not flush with a bottom surface of the sheath member.

19. The sensor probe of claim 1 wherein the sheath member comprises an elastomeric material comprising at least an outside back surface, opposite to the inside surface, that is coupled to four outside side surfaces,
  the sheath member comprises four inside side surfaces coupled to the inside surface of the opening of the recessed region,
  each of the four inside side surfaces is opposite to the four outside side surfaces,
  the four outside side surfaces surround the scanning surface of the sensor unit, and
  in the four outside and inside side surfaces is the elastomeric material without prefabricated suture openings extending through the elastomeric sheath member.

20. The sensor probe of claim 19 wherein a first side of the four outside side surfaces is transverse to a second side of the four outside side surfaces.

21. The sensor probe of claim 1 wherein the elastomeric material has a durometer shore A hardness in a range from about 30 to about 70, and the sensor probe further comprises:
  an adhesive having elasticity, coupled between the sensor unit and the inside surface of the sheath member.

22. The sensor probe of claim 1 further comprising the first tubing sleeve covering the first portion of the cable nearby the sensor unit; and
  the second tubing sleeve, separated from the first tubing sleeve, covering the second portion of the cable farther away from the sensor unit than the first tubing sleeve, wherein the first and second tubing sleeves comprise solid elastomeric material.

23. The sensor probe of claim 1 wherein the elastomeric sheath member is elongated in at least one direction to allow removal of the sensor unit from the elastomeric sheath member.

24. The sensor probe of claim 1 wherein portions of at least three edges of the elastomeric sheath member are adapted for suturing the sensor unit onto tissue.

25. The sensor probe of claim 1 wherein when the elastomeric sheath member is sutured onto tissue, the elastomeric sheath member is used to hold the sensor unit onto the tissue for the sensor unit to evaluate the tissue.

26. The sensor probe of claim 1 wherein a region of the elastomeric sheath member that comprises the solid translucent material is pierced when suturing the sensor probe.

27. The sensor probe of claim 26 wherein the region of the elastomeric sheath member adapted for suturing the sensor unit onto tissue is approximately the same or greater than the thickness of the sensor unit.

28. The sensor probe of claim 1 wherein the elastomeric material is sutured onto the tissue without piercing the recessed region.

29. The sensor probe of claim 1 wherein the lip region comprises walls forming the recessed region adapted to allow a surgical needle to thread a top surface to a bottom surface of the lip region to secure the sensor unit onto the tissue.

30. The sensor probe of claim 1 wherein the first tubing sleeve is adapted to protect one or more glass fibers housed in the cable from a patient's biting force while the solid translucent material is sutured.

31. The sensor probe of claim 30 wherein the thickness of the tubing sleeve is approximately 2.38 millimeters.

32. The sensor probe of claim 1 wherein the first and second tubing sleeve portions are slidably coupled to the cable.

33. The sensor probe of claim 32 wherein the first tubing sleeve portion comprises an elastomeric material that can be sutured.

34. The sensor probe of claim 32 wherein the second tubing sleeve portion is adapted to protect the at least two optical fibers within the cable from a biting force.

35. The sensor probe of claim 1 wherein the solid translucent material is adapted for suturing by piercing the solid translucent material through the first pierceable surface with a suture in a first direction, exiting the solid translucent material through the second pierceable surface with the suture in the first direction, and attaching the suture to the tissue.

36. The sensor probe of claim 35 wherein the solid translucent material is adapted for suturing by, after attaching the suture to the tissue, piercing the solid translucent material through the second pierceable surface with the suture in a second direction, exiting the solid translucent material through the first pierceable surface with the suture in the second direction; and securing the suture onto itself.

37. The sensor probe of claim 35 wherein the solid translucent material is adapted for suturing by, after attaching the suture to the tissue, securing the suture onto itself without piercing the solid translucent material.

38. A sensor probe comprising:
a sensor unit comprising a rectangular scanning surface, a rectangular back surface, opposite the rectangular scanning surface, and a thickness of the sensor unit is between the scanning and back surfaces,
wherein the rectangular scanning surface comprises a first source structure and a first detector structure, wherein the rectangular scanning surface comprises a first edge extending in a first direction and a second edge extending in a second direction, wherein the second edge is adjacent to the first edge, the first direction is perpendicular to the second direction, and the first edge is longer than the second edge,
the sensor unit comprises a metal housing,
the first source structure comprises a first optical fiber, and
the first detector structure comprises a second optical fiber;
an elastomeric sheath member comprising a first rectangular surface, a second rectangular surface opposite the first rectangular surface, a lip region, and a thickness of the translucent elastomeric sheath member is between the first and second rectangular surfaces,
wherein the elastomeric sheath member comprises an elastomeric material having greater elasticity than the metal housing of the sensor unit,
the first rectangular surface comprises a rectangular opening coupled to a recessed region of the elastomeric sheath member for embedding the sensor unit, and the lip region surrounding the rectangular scanning surface of the sensor unit comprises a translucent material that is pierced to attach the sensor unit onto a patient's tissue, wherein the rectangular opening comprises an opening length in the first direction that is longer than an opening width in the second direction, the opening length and the first edge of the scanning surface have the same length, and the opening width and the second edge of the scanning surface have the same width,
the recessed region comprising an inside surface, opposite to the rectangular opening, a first wall extending in the first direction, a second wall adjacent to the first wall, extending in the second direction, and a thickness between a plane of the opening and the inside surface, wherein the thickness of the recessed region is less than the thickness of the elastomeric sheath member, and an area of the inside surface is the same as an area of the rectangular back surface of the sensor unit,
the lip region is adapted for suturing from a pierceable surface of the lip region through the thickness of the recessed region to an opposite pierceable surface of the lip region, without piercing the first or second walls, on a patient's tissue to hold the sensor unit to the patient's tissue,
the back surface of the sensor unit is positioned against the inside surface of the recessed region,
the scanning surface of the sensor unit comprising the first source structure and first detector structure faces in a direction away from the inside surface,
whereby when the scanning surface is placed against a tissue to be evaluated, the inside surface of the recessed region urges, via the back surface, the scanning surface of the sensor unit flush against the tissue, and
the elastomeric sheath member further comprising an internal channel extending from the second wall of the recessed region to an end of the elastomeric sheath member, wherein the internal channel comprises a rectangular cross section;
a rectangular cable connected to the sensor unit wherein the cable is placed in the internal passageway of the elastomeric sheath member, and is configured to operably couple the sensor unit to a system unit;
a first tubing sleeve portion enclosing a first exterior surface of the cable; and
a second tubing sleeve portion enclosing a second exterior surface of the cable,
wherein the first tubing sleeve portion is located adjacent but separate from the elastomeric sheath member and the second tubing sleeve portion is located adjacent but separate from the first tubing sleeve portion.

39. The sensor probe of claim 38 wherein the thickness of the lip region in a first direction is approximately the same or greater than the thickness of the sensor unit in the first direction.

40. A sensor probe comprising:
a sensor unit comprising a first source structure and a first detector structure on a scanning surface of the sensor unit;
an elastomeric sheath member having a recessed region for embedding the sensor unit and a lip region surrounding the scanning surface of the sensor unit,
wherein the elastomeric sheath member comprises an elastomeric material having greater elasticity than the sensor unit and the elastomeric sheath member comprises a solid translucent material, without prefabricated suture openings extending through, adapted for suturing the elastomeric sheath member with the sensor unit onto tissue,
the recessed region comprises an opening and an inside surface, opposite to the opening,
the scanning surface of the sensor unit comprising the first source structure and first detector structure faces in a direction away from the inside surface,
the solid translucent material is designed to be sutured onto tissue without having sutures entering the recessed region where the sensor unit is embedded,
at a first time when the solid translucent material is sutured, the first source structure and first detector structure of the scanning surface are placed against a tissue to be evaluated, the first source structure emits a first light into the tissue without passing through the elastomeric sheath member, and the first detector structure receives a second light reflected from the tissue, and
at a second time when the solid translucent material is sutured and during a recovery period after surgery, the first source structure and first detector structure of the scanning surface placed against the tissue to be evaluated, the first source structure emits a third light into the tissue without passing through the elastomeric sheath member, and the first detector structure receives a fourth light reflected from the tissue;
a cable connected to the sensor unit wherein the cable is configured to operably couple the sensor unit to a system unit;
a display wherein the display indicates oxygen saturation levels at the first time and second time;
a first tubing sleeve portion enclosing a first exterior surface of the cable; and
a second tubing sleeve portion enclosing a second exterior surface of the cable, wherein the first tubing sleeve portion is located adjacent but separate from the elastomeric sheath member and the second tubing sleeve portion is located adjacent but separate from the first tubing sleeve portion.

41. The sensor probe of claim 40 wherein the surgery comprises a tissue transplantation procedure and the first time comprises when the tissue to be evaluated is intact at a donor site.

42. The sensor probe of claim 41 wherein the second time comprises when the tissue to be evaluated is at a recipient site after the surgery.

* * * * *